US009968669B2

(12) United States Patent
Schmaljohn

(10) Patent No.: US 9,968,669 B2
(45) Date of Patent: May 15, 2018

(54) GENE OPTIMIZED HANTAAN VIRUS M SEGMENT DNA VACCINE FOR HEMORRHAGIC FEVER WITH RENAL SYNDROME

(71) Applicant: The United States of America, as represented by the Secretary of the Army, Washington, DC (US)

(72) Inventor: Connie Schmaljohn, Middletown, MD (US)

(73) Assignee: The United States of America, as represented by the Secretary of the Army, Washington, DC (US)

( * ) Notice: Subject to any disclaimer, the term of this patent is extended or adjusted under 35 U.S.C. 154(b) by 0 days. days.

(21) Appl. No.: 15/400,028

(22) Filed: Jan. 6, 2017

(65) Prior Publication Data

US 2017/0112916 A1    Apr. 27, 2017

Related U.S. Application Data

(60) Division of application No. 14/756,608, filed on Sep. 24, 2015, now Pat. No. 9,675,684, which is a continuation of application No. PCT/US2013/000098, filed on Mar. 28, 2013.

(51) Int. Cl.

| A61K 39/12 | (2006.01) |
|---|---|
| C12N 7/00 | (2006.01) |
| C07K 14/005 | (2006.01) |
| A61K 9/12 | (2006.01) |
| A61K 9/51 | (2006.01) |
| A61K 9/00 | (2006.01) |
| A61K 39/385 | (2006.01) |
| A61K 39/00 | (2006.01) |

(52) U.S. Cl.
CPC ............ *A61K 39/12* (2013.01); *A61K 9/0009* (2013.01); *A61K 9/0019* (2013.01); *A61K 9/0021* (2013.01); *A61K 9/0073* (2013.01); *A61K 9/12* (2013.01); *A61K 9/51* (2013.01); *A61K 9/5115* (2013.01); *A61K 39/385* (2013.01); *C07K 14/005* (2013.01); *C12N 7/00* (2013.01); *A61K 2039/53* (2013.01); *A61K 2039/575* (2013.01); *A61K 2039/70* (2013.01); *C12N 2760/12122* (2013.01); *C12N 2760/12134* (2013.01); *C12N 2760/12171* (2013.01); *C12N 2800/22* (2013.01)

(58) Field of Classification Search
None
See application file for complete search history.

(56) References Cited

U.S. PATENT DOCUMENTS

| 5,853,980 A | 12/1998 | Rollin et al. |
|---|---|---|
| 5,945,277 A | 8/1999 | Nichol et al. |
| 7,217,812 B2 | 5/2007 | Hooper |
| 2010/0323024 A1 | 12/2010 | Hooper |

FOREIGN PATENT DOCUMENTS

| EP | 2520562 A1 | 7/2012 |
|---|---|---|
| EP | 1529107 B1 | 10/2012 |

OTHER PUBLICATIONS

Schmaljohn, Vaccines for hantaviruses, 2009, Vaccine, vol. 27, pp. D61-D64.*
Chu, Serological relationships amound viruses n the Hantavirus genus, family Bunyaviridae, Virology 994; 198 (Jan. (1): 196-204.
Fuller DH et al., Preclinical and clinical progress of particle mediated DNA vaccine . . . , Methods 2006:40 (Sep. (a)):86-87.
Hooper et al., Hantaan/Andes virus DNA vaccine elicits a broadly cross-reactive . . . , Viroloty 2006:347 (Mar. (1)):208-16.
Spik et al., Mixing M segment DNA vaccines to Hantaan virus . . . , Vaccine 2008; 26 (Sep. (40)):5177-81.
Sheshberadaran, et al, Antigenic relationskp between hantaviruses analysed by immunoprecipitation, J. Gen. Virol. 1988;69 (Mar. (Pt10);2645-51.
Arikawa, et al., Characterization of Hantaan virus envelope glycoprotein antigenic . . . , J. Gen. Virol 1989;70(Mar.(Pt3));615-24.
Brocato, et al., 2013, Construction and nonclinical testing of a puumala virus synthetic M gene-based DNA vaccine., Clin Vaccine Immunol 20(2):218-226.
NCBI, GenBank Acession No. HI424342.1 (Nov. 9, 2010) whole document.
NCBI, GenBank accession No. DI004188.1 (Feb. 21, 2008) whole doc.
Boudreau, EF, et al., A phae 1 clinical trial Hantaan virus and Puumala virus M-segment, DNA vaccines . . . , Vaccine Mar. 2, 2012, vol. 30, No. 11, 1951-58.
Schmaljohn CS, et al.Antigenic subunits of Hanaan virus expressed by baculovirus and vaccinia virus recombinants. J. Virol 1990; 64(Jul.(7)):3162-70.
Custer, et al., Active and passive vaccination against hantavirus pulmonary syndrome and Dndesvirus M genome . . . , J virol 2003;77(Sep.(18)):9894-905.
Hooper, et al. DNA vaccination with hantavirus M segment elicits neutralizing antibodies and protects against Seoulvirus infection, Virology 1999;255(Mar.(2)):269-78.
Schmaljohn C, Naked DNA vaccines expressing the prM and E genes of Russian spring summer encephalitis virus . . . ; J Virol 1997;71(Dec.(12)):9563-9.

(Continued)

*Primary Examiner* — Benjamin P Blumel
(74) *Attorney, Agent, or Firm* — Elizabeth Arwine

(57) ABSTRACT

A synthetic, codon-optimized Hantaan virus (HTNV) full-length M gene open reading frame that consists of a unique nucleotide sequence encoding HTNV proteins. This synthetic gene was cloned into a plasmid to form the first optimized HTNV full-length M gene that elicits neutralizing antibodies in animals when delivered in combination with a similarly optimized Puumala virus (PUUV) DNA vaccine. The invention obviates the need for an extraneous gene sequence that was previously required for expression of the non-optimized HTNV gene. The synthetic gene is engineered into a molecular vaccine system to prevent hemorrhagic fever with renal syndrome (HFRS) caused by infection with HTNV, SEOV, or DOBV. Alternatively, it can be combined with the optimized PUUV DNA vaccine to protect against HFRS caused by any hantavirus.

3 Claims, 27 Drawing Sheets

(56) References Cited

OTHER PUBLICATIONS

Roy MJ, et al., Induction of antigen specific CD8+ T cells, T helper cells . . . , Vaccine 2000;19(Nov. (7-8)):764-78.
Roberts LK, et al., Clinical safety and efficacy of a powdered hepatitus B nucleic acid vaccine . . . , Vaccine 2005;23(Sep. (40)):4867-78.
Badger CV, et al., Development and application of a flow cytometric potency assay for DNA vaccines, Vaccine 2011; (Jan.):6728-35.
Rossi CA, et al., Enzyme-linked immunoborbent assay (ELISA). Asan Institute for Life Sciences; 1999. p. 87-98.
Schmaljohn, et al., Antegenic and genetic properties of viruses linked to hemorrhagic fever with renal syndrome., Science 1985; 227(Mar. (4690)):1041-4.
Chu, et al. Cross-neutralization of hantaviruses with immune sera from experimentally infected animals and from hemrrhagic . . . , J Infect Dis 1995;172(Dec.(6)):1581-4.
Hooper JW, Vaccine against hantaviruses, Curr Top Microbiol Immunol 2001 ; 256:171-91.
Maes, P., et al., Recent approaches in hantavirus vaccine development, Expert Rev Vaccines 2009;8(Jan. (1))):67-76.
Wang, et al. Epidemiology and Surveillance programs on hemorrhagic.., Zhonghua Liu Xing Bing Xue Za Zhi 2010;31(Jun. (6)):675-80.
Fang, et al. Spatiotemporaltrends and climatic factors of hemorrhagic . . . , PLoS Negl Trop dis 2010:4(8):e789.
Zhang YZ et al., Hantavirus infections in humans and animals, China Emerg Infect Dis Aug. 2010:16(Aug.(8)):1195-203.
Heyman, Situation of hantavirus infections and haemorrhagic fever . . . , Dec. 2006, Euro Surveill 2008;13(Jul.(28)).
Chu YK, et al., A vaccinia virus-vectored Hantaan virus vaccine protects.., J. Virol 1995; 69 (Oct. (10)):6417-23.
Hooper JW, et al., DNA vaccination with the Hantaan virus M gene protects hamsters . . . , J. Virol 2001:75 (Sep. (18)):8469-77.
McClain DJ, et al., Clinical evaluation of a vaccinia-vectored Hantaan virus vaccine, J. Med Virol 2000: 60(Jan. (1)):77-85.
Schmaljohn CS, et al., Preparation of candidate vaccinia-vectored vaccines for haemorrhagic fever with renal syndrome. Vaccine 1992:10(1):10-3.
Hooper, et al, 2014,A Phase I clinical trial of Hantaan virus and Puumala virus M-segment DNA vaccines for haemorrhagic fever.., CMI 10.1111/1469-0691.12553.
Schmaljohn, et al, 2014, DNA vaccines for HFRS: Laboratory and clinical studies, Virus Research 187, 91-96.

\* cited by examiner

```
                    ┌─────────────────────────┐
                    │  Open label, single center │
                    │    Adults age 18-50      │
                    │        N = 28*           │
                    └─────────────────────────┘
          ┌──────────────────┬──────────────────┐
┌─────────────────┐  ┌─────────────────┐  ┌─────────────────┐
│ Subjects in Group 1a│  │ Subjects in Group 2a│  │ Subjects in Group 3a│
│   HTNV Vaccine   │  │   PUUV Vaccine   │  │ HTNV-PUUV Vaccines│
│      n = 3       │  │      n = 3       │  │      n = 3       │
│ (ID 0001,0003*, 0005,│ (ID 0002,0004, 0006)│ (ID 0007, 0008, 0010)│
│      0009)       │  │                  │  │                  │
└─────────────────┘  └─────────────────┘  └─────────────────┘
┌─────────────────┐  ┌─────────────────┐  ┌─────────────────┐
│ Subjects in Group 1b│  │ Subjects in Group 2b│  │ Subjects in Group 3b│
│   HTNV Vaccine   │  │   PUUV Vaccine   │  │ HTNV-PUUV Vaccines│
│      n = 6       │  │      n = 6       │  │      n = 6       │
│ (ID 0011, 0013, 0017,│ (ID 0012, 0014, 0016,│ (ID 0015, 0018, 0019,│
│  0021, 0025, 0029)│ │  0022, 0026, 0028)│ │  0020, 0024, 0027)│
└─────────────────┘  └─────────────────┘  └─────────────────┘
                    ┌─────────────────────────┐
                    │ Subjects Completing      │
                    │ HTNV-PUUV Vaccine        │
                    │       Study              │
                    │       N = 27             │
                    └─────────────────────────┘
```

FIG. 1

PUUV Vaccination
- ■ 0026 (PUUV)
- □ 0026 (HTNV)

HTNV Vaccination
- ● 0029 (PUUV)
- ○ 0029 (HTNV)

HTNV M  HTNV M(x)

PUUV PRNT

```
     5000
     4000
GMT PRNT50
     3000
     2000
     1000
          IM   ID   IM      IM   ID   IM
          ─────────────      ─────────────
              PUUV            1:1 HTNV:PUUV
```

Cohort 1: HTNV vaccine
7 of 11 seroconverted to HTNV

FIG. 12A

Cohort 2: PUUV vaccine
6 of 8 seroconverted to PUUV

FIG. 12B

Cohort 3: Combination HTNV/PUUV vaccines - 7 of 9 seroconverted
(3 to HTNV, 7 to PUUV, 3 to both)

FIG. 12C

Cohort 3: Combination HTNV/PUUV vaccines - 7 of 9 seroconverted
(3 to HTNV, 7 to PUUV, 3 to both)

FIG. 12D

| Group # | # of Subjects | Vaccine | Dose (mg) | Volume (ml) | Schedule (Days) |
|---|---|---|---|---|---|
| 1 | 30 | HTNV/PUUV | 2.0 | 1.0 | 0, 28, 56 (180) |
| 2 | 30 | HTNV/PUUV | 2.0 | 1.0 | 0, 56 (180) |
| 3 | 30 | HTNV/PUUV | 1.0 | 1.0 | 0, 28, 56 (180) |
| 4 | 30 | HTNV/PUUV | 1.0 | 1.0 | 0, 56 (180) |
| total | 120 | | | | |

GENE OPTIMIZED HANTAAN VIRUS M SEGMENT DNA VACCINE FOR HEMORRHAGIC FEVER WITH RENAL SYNDROME

This application claims priority and is a divisional application of U.S. Ser. No. 14/756,608 filed Sep. 24, 2015 which is a continuation of PCT/2013/000098 filed Mar. 28, 2013.

GOVERNMENT INTEREST

The invention described herein may be manufactured, used and licensed by or for the U.S. Government.

BACKGROUND OF THE INVENTION

The invention relates to a vaccine for hemorrhagic fever with renal syndrome caused by hantavirus infections.

The *Hantavirus* genus of the family Bunyaviridae includes a number of rodent-borne viruses that can cause hemorrhagic fever with renal syndrome (HFRS) or hantavirus pulmonary syndrome (HPS). At least four hantaviruses cause HFRS: Hantaan (HTNV), Seoul (SEOV), Dobrava (DOBV), and Puumala (PUUV) viruses. HFRS presents with sudden fever, chills, nausea, headache, and backache. Early symptoms of severe HFRS often also include facial flushing, conjunctivitis, and petechial rash. Death can occur due to vascular leakage leading to low blood pressure, acute shock, and renal failure. There are no FDA-licensed vaccines for HFRS, but an inactivated, rodent-brain-derived HTNV vaccine is commercially available in Korea, and several inactivated cell culture-derived HTNV and SEOV vaccines have been developed in China [1,2].

Despite the use of these vaccines for more than a decade, HFRS remains a significant public health threat in Asia with thousands of hospitalized cases reported each year in China [3-5]. Several hundred to thousands of HFRS cases due to PUUV or DOBV infections are reported each year in Europe, Scandinavia, and Russia, with the greatest incidences observed in Finland (~25,000 cases from 1979 to 2006) and western Russia (~89,000 cases from 1996 [6]. Inactivated vaccines have not been developed in Europe, in part because PUUV is difficult to grow in cell culture to high enough titers for scale-up, and rodent brain-derived vaccines are not considered desirable. Moreover, because DOBV and PUUV both cause HFRS in the same geographic region, and because there is little or no cross-protective immunity between PUUV and the other HFRS-causing hantaviruses [7,8], a comprehensive vaccine for European HFRS will need to elicit protective immunity to both viruses.

To date, two recombinant DNA vaccines for HFRS have been tested in early clinical studies. The first tested was a vaccinia virus (VACV)-vectored vaccine, developed and evaluated in Phases 1 and 2 clinical studies by USAMRIID [9,10]. The vaccine expressed two of the three gene segments of HTNV: the M segment, which encodes the envelope glycoproteins (Gn and Gc), and the S segment, which encodes the nucleocapsid protein (N). In general, animal studies have shown that neutralizing antibodies to Gn and Gc are the best measurable correlate of protective immunity [8, 11-13]. This earlier study found that the recombinant VACV vaccine elicited neutralizing antibodies against HTNV in VACV-naïve individuals, but was poorly immunogenic in VACV-immune volunteers [9]. Consequently, the vaccine developers changed strategies to a DNA vaccine platform, which was not adversely affected by preexisting vector immunity and which offered additional flexibility for producing combination vaccines. In addition to flexibility, DNA is an attractive vaccine platform in terms of ease of engineering and manufacturing as well as safety.

USAMRIID investigators have so far conducted two Phase 1 clinical studies with DNA vaccines for HFRS using DNA derived from HTNV and from PUUV M segments. The two-part DNA vaccine strategy was used because vaccination with the HTNV M gene-based DNA vaccine protects animals from infection with HTNV, DOBV and SEOV, but not from PUUV infection. PUUV M gene-based DNA vaccine protects against infection with PUUV [7-8].

The first two clinical studies of the HTNV and PUUV DNA vaccines were performed using a PUUV M segment vaccine that was genetically optimized (US 2010/0323024A1, incorporated herein by reference in its entirety). The HTNV component, however, was not optimized, because unlike the PUUV DNA, which required optimization for gene expression, the HTNV DNA construct showed strong gene expression without optimization. It could not be anticipated, therefore, that a similar optimization was either necessary or would offer a benefit over the non-optimized DNA for immunogenicity. Further and formerly, an extraneous gene sequence was required for the expression of the non-optimized HTNV gene, U.S. Pat. No. 7,217,812, incorporated by reference, herein, in its entirety.

In the first clinical study of the DNA vaccines, HTNV and PUUV M segments were delivered by particle mediated epidermal delivery (PMED). The advantage of intraepidermal delivery of the vaccine is twofold. The DNA is easily taken up by cells at the site of delivery or by cells in the draining lymph nodes where the antigen encoded by those cells is reprocessed by specialized antigen-presenting cells to elicit an immune response, and this approach uses 1000-fold less DNA than needle administration.

The vaccines were given as separate administrations because of results from animal studies, which showed that if the HTNV vaccine is mixed with the PUUV vaccine, then only neutralizing antibodies to PUUV are elicited [25]. This finding was not expected, because it was possible to obtain strong responses to the individual vaccines or to both vaccines when they were delivered simultaneously, but as separate inoculations, to a single animal. In addition, it was not possible to overcome this interference by adjusting the ratio of HTNV: PUUV DNA even as high as 10:1 (FIG. 8B). Other attempts to produce modified constructs that were chimeras of both the HTNV and PUUV genes also failed to elicit antibody responses to both HTNV and PUUV (unpublished information). The outcome of the interference study is summarized in Example 1.

In a second Phase 1 clinical study of the same two DNA vaccines, the DNAs were given separately or as a mixture by intramuscular electroporation (IM-EP). With this delivery method, the vaccines are injected into muscles and a rapid electrical pulse is applied to facilitate uptake of the DNA into the muscle cells. Because a larger number of host cells receive the vaccines than when they are delivered by PMED, it was anticipated that there might be some response to both vaccines. As expected, however, interference was still a problem in individuals receiving the mixed vaccines, with better responses obtained to the PUUV vaccine than to the HTNV vaccine as shown in Example 2.

Delivery of the vaccine can also be by nanoparticle encapsulation of the vaccine via various methods, including aerosol delivery of the nanoparticles.

The present invention provides a combination vaccine to protect against HFRS. The invention consists of an optimized HTNV M segment vaccine, which solves the problem of interference in the bivalent vaccine. Unlike the non-optimized HTNV vaccine used in previous studies, the vaccine of the invention can be mixed with a similarly optimized PUUV-based vaccine to elicit neutralizing antibodies against both viruses. The invention provides a safe, economical, flexible and effective vaccine for the protection of humans from HFRS caused by infection with HTNV, SEOV, PUUV and/or DOBV.

SUMMARY OF THE INVENTION

The invention is a synthetic, optimized HTNV M segment DNA vaccine that is superior to the earlier non-optimized HTNV DNA vaccine and can be used by itself to prevent HFRS caused by three hantaviruses: (HTNV, SEOV or DOBV) or in combination with the optimized PUUV DNA vaccine to protect from all four HFRS causing hantaviruses. The synthetic optimized HTNV DNA does not require extraneous, superfluous nucleotides for expression and immunogenicity and can be delivered as a mixture with other hantavirus vaccines without reduced immunogenicity or protective efficacy in animal models. To improve the vaccine component, the HTNV DNA vaccine was optimized to maximize mammalian codon availability and to remove viral elements shown to compromise expression.

BRIEF DESCRIPTION OF THE FIGURES

FIG. 1 is a flowchart showing a Phase 1 clinical study design wherein all vaccinations with the non-optimized HTNV DNA vaccine and the optimized PUUV DNA vaccine were administered intradermally using the ND 10 PMED device;

FIG. 3 is a graph showing neutralizing antibodies in blood samples collected on multiple days from two subjects vaccinated with either the optimized PUUV vaccine (subject 0026) or the non-optimized HTNV vaccine (subject 0029) with each symbol representing the neutralizing antibody (PRNT$_{50}$) titer for subjects listed in the legend and arrows indicating vaccination days, The graph shows that the optimized PUUV vaccine induced neutralizing antibodies to PUUV (closed squares) but not to HTNV (open squares). Likewise, the non-optimized HTNV vaccine induced antibodies to HTNV (open circles), but did not cause a rise in antibodies to PUUV (closed circles) even though the subject had low pre-existing antibodies to PUUV (dashed line).

Figures 4A, 4B:
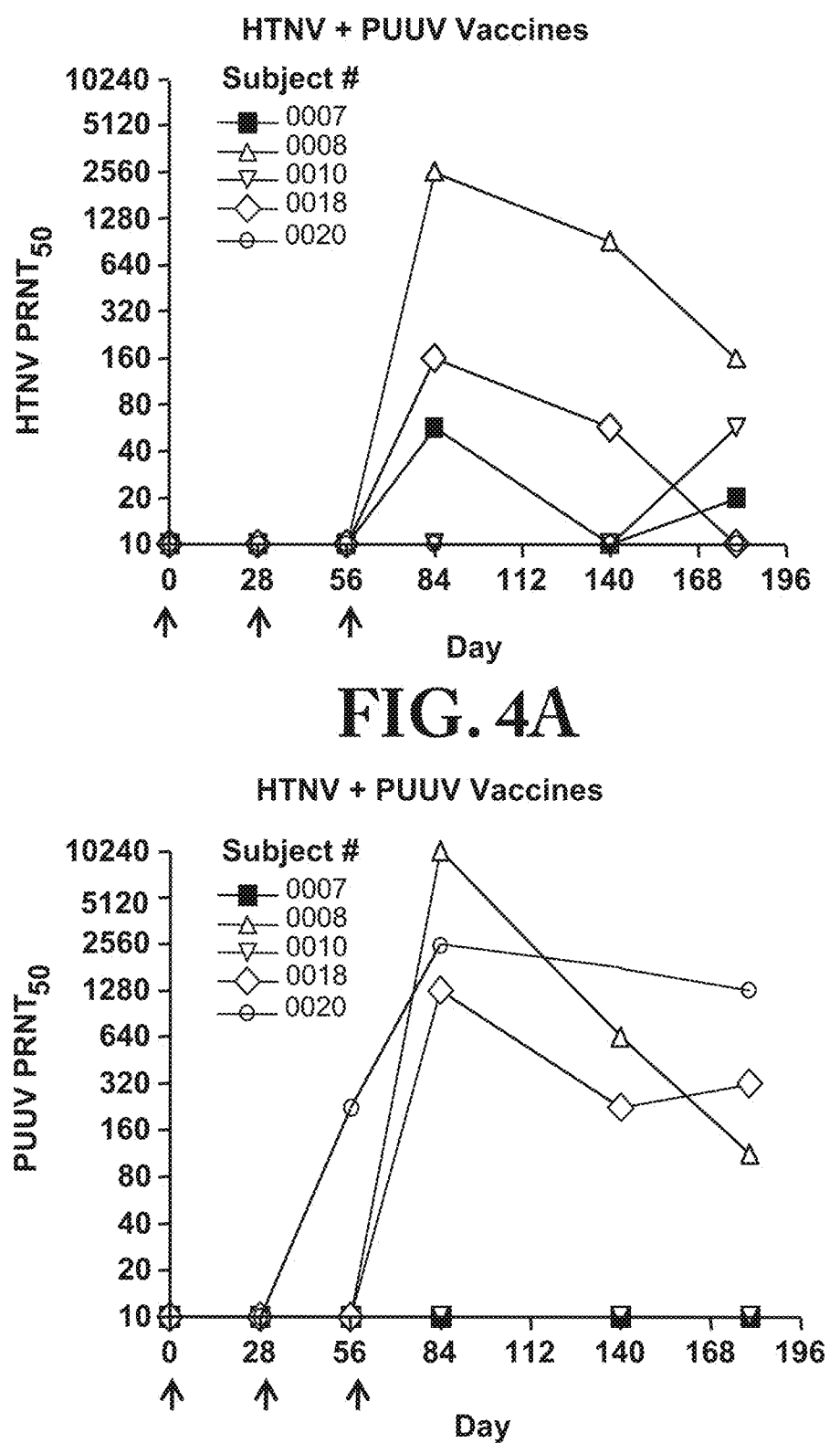

FIG. 4A is a graph showing neutralizing antibody responses to HTNV of subjects receiving separate administrations of the non-optimized HTNV DNA vaccine and the optimized PUUV vaccine with each symbol representing the neutralizing antibody (PRNT$_{50}$) titer for subjects listed in the legend and arrows indicating vaccination days, showing that separate administrations of both the HTNV and PUUV DNA vaccines to a single individual can induce antibody responses to HTNV;

FIG. 4B is a graph showing neutralizing antibody responses to PUUV of subjects receiving separate administrations of the non-optimized HTNV DNA vaccine and the optimized PUUV vaccine with each symbol representing the PRNT$_{50}$ titer for subjects listed in the legend and arrows indicating vaccination days, showing that separate administrations of both the HTNV and PUUV DNA vaccines to a single individual can induce antibody responses to PUUV;

FIG. 7A is a digital photograph showing HTNV protein (green color) produced by the optimized HTNV M segment vaccine (HTNV M) and detected by immunofluorescent antibody staining with a monoclonal antibody to HTNV;

FIG. 7B is a digital photograph showing HTNV protein (green color) produced by the non-optimized HTNV M segment vaccine (HTNV M (x)) and detected by immunofluorescent antibody staining with a monoclonal antibody to HTNV;

FIG. 7C is a graph from a flow cytometry assay showing expression of the optimized HTNV M segment DNA synthesized to also contain the extraneous nucleotides found in the non-optimized HTNV M vaccine as compared to the same DNA synthesized without the extraneous sequences;

FIG. 7D is a graph from a flow cytometry assay showing expression of the synthetic optimized HTNV M segment DNA compared to the non-optimized DNA;

FIG. 8A is a graph showing neutralizing antibodies to PUUV of hamsters vaccinated with the optimized PUUV DNA vaccine or a 1:1 mixture of the optimized PUUV vaccine and the non-optimized HTNV using two types of IM-EP devices or one type of intradermal (ID) EP device, showing that HTNV DNA does not interfere with PUUV DNA immunogenicity;

FIG. 8B is a graph showing neutralizing antibodies to HTNV of hamsters vaccinated with the non-optimized HTNV DNA vaccine alone, the optimized PUUV DNA vaccine alone or 1:1, 2:1 or 10:1 mixtures of the non-optimized HTNV DNA and the optimized PUUV DNA vaccines using two types of intramuscular IM-EP devices or one type of ID-EP device, showing that PUUV DNA does interfere with HTNV DNA immunogenicity;

FIG. 9 is a graph showing immunogenicity (specific neutralizing antibodies) in hamsters of optimized HTNV DNA vaccine of the invention compared to the non-optimized HTNV DNA, the optimized PUUV DNA vaccine or a 1:1 mixture of both optimized DNA vaccines delivered to hamsters by ID-EP, showing that the optimized HTNV DNA has overcome interference problems associated with the non-optimized HTNV DNA;

FIG. 10 is a graph showing the immunogenicity (neutralizing antibodies to HTNV) in hamsters vaccinated by electroporation with the optimized HTNV DNA vaccine alone, a 1:1 mixture of the optimized HTNV and PUUV DNA vaccines, or the optimized PUUV DNA vaccine alone after each of three sequential vaccinations, indicating that the optimized HTNV vaccine and the mixture of the optimized HTNV and PUUV DNA vaccines induce neutralizing antibodies to HTNV, but that the optimized PUUV DNA vaccine alone does not elicit neutralizing antibodies to HTNV.

FIG. 11B is a graph showing neutralizing antibodies to HTNV of individual rabbits vaccinated by IM-EP with non-optimized HTNV DNA vaccine (pWRG/HTN-M(x) as compared to the PUUV DNA vaccine (pWRG/PUU-M(s2) or a mixture of the two vaccines (Combination) showing evidence of interference;

FIG. 12A is a graph showing neutralizing antibody responses to HTNV of humans vaccinated with the non-optimized HTNV DNA vaccine by IM-EP;

FIG. 12B is a graph showing neutralizing antibody responses to PUUV of humans vaccinated with the optimized PUUV DNA vaccine by IM-EP;

FIG. 12C is a graph showing neutralizing antibody responses to HTNV of humans vaccinated with a 1:1 mixture of non-optimized HTNV and optimized PUUV DNA vaccines by intramuscular electroporationIM-EP; indicating reduced number of responses to HTNV and evidence of interference with HTNV immunogenicity.

FIG. 12D is a graph showing neutralizing antibody responses to PUUV of humans vaccinated with a 1:1 mixture of non-optimized HTNV and optimized PUUV DNA vaccines by intramuscular electroporationIM-EP; indicating no interference with PUUV immunogenicity.

FIG. 14 is a table showing a study design for an ongoing clinical study in 120 subjects vaccinated with two doses and at two schedules by IM-EP with the mixed optimized HTNV and PUUV DNA vaccines;

DETAILED DESCRIPTION

A recombinant DNA-based vaccine for HTNV and PUUV M segments constructs circumvents key issues associated with both production and formulation of combination vaccines for HFRS. The invention provides a bivalent vaccine for all HFRS-causing viruses, which includes both HTNV and PUUV M segment constructs.

The invention is a new synthetic, codon-optimized HTNV full-length M gene open reading frame (ORF) that encodes amino acids forming viral proteins. The optimization of the gene has solved a long felt need in this type of vaccine, namely major gene related interference with former vaccines, which prevented development of a comprehensive vaccine for HFRS. Determining how to optimize and produce a synthetic gene for the HTNV M segment required extensive testing.

This synthetic gene was cloned into a plasmid to form the first HTNV full-length M gene that elicits neutralizing antibodies in animals when delivered in combination with a similarly optimized PUUV DNA vaccine (U.S. patent publication US2010/0323024A1, incorporated herein by reference). In addition, the invention obviates the need for an extraneous gene sequence that was previously found to be required for expression of the non-optimized HTNV gene. The synthetic gene is engineered into a molecular vaccine system to prevent HFRS caused by infection with HTNV, SEOV or DOBV. Alternatively, it can be combined with the optimized PUUV DNA vaccine to protect against HFRS caused by any hantavirus.

Specifically, the invention consists of a genetically modified DNA vaccine representing the open reading frame of the M genome segment of the HTNV that has been optimized to include several features known to increase mammalian expression. See SEQ ID NO. 1

Figure 2A:
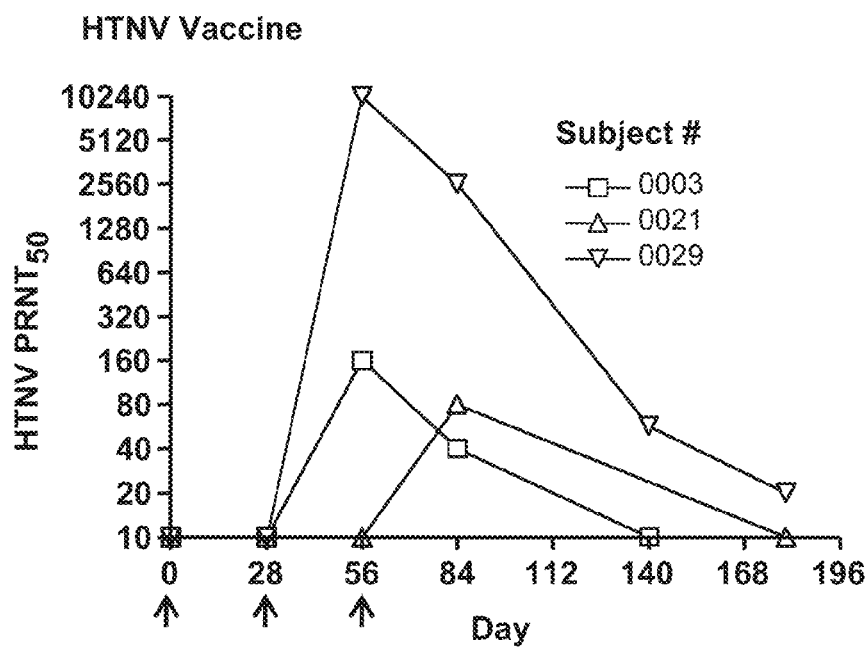
FIG. 2A is a graph of neutralizing antibody titers measured in serum samples collected from subjects vaccinated with the non-optimized HTNV vaccine.
Figure 2B:
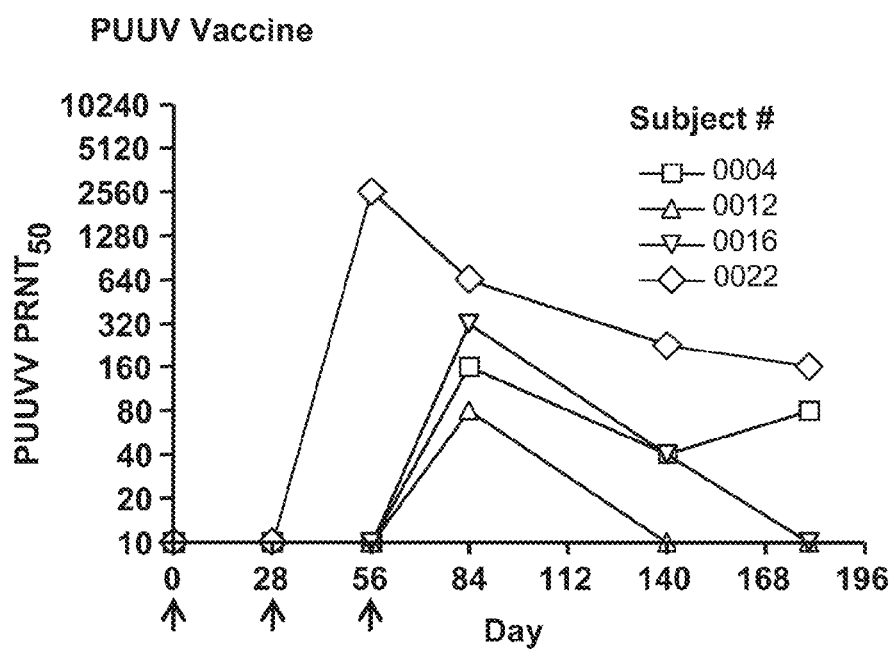
FIG. 2B is a graph of neutralizing antibody titers measured in serum samples collected from subjects vaccinated with the optimized PUUV vaccine.
Figure 5:
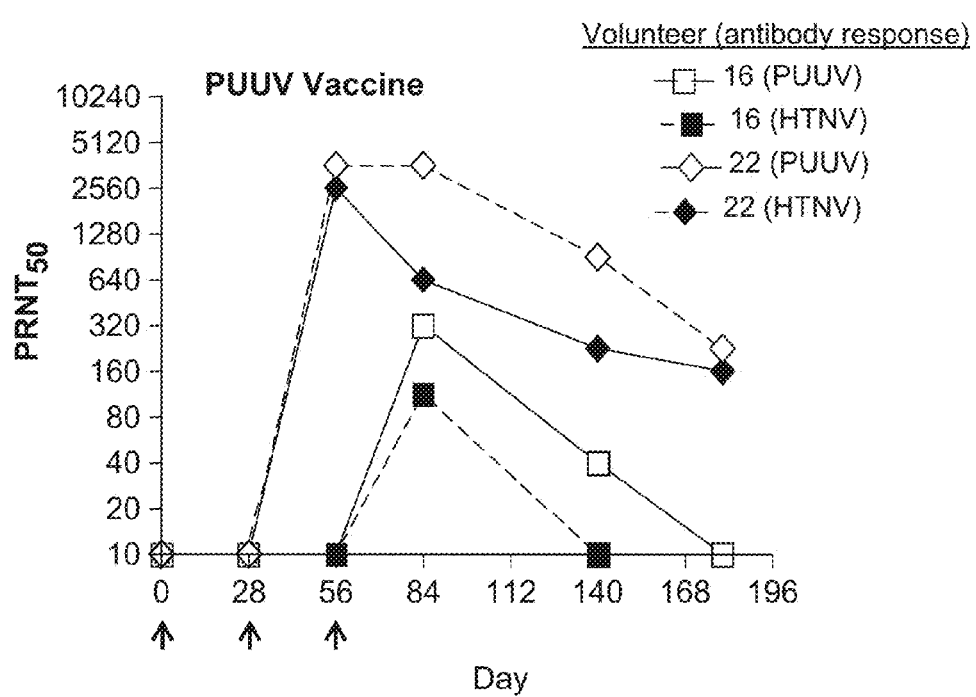
FIG. 5 is a graph showing two individuals vaccinated with the optimized PUUV DNA that developed antibodies to both HTNV and PUUV.
Figure 6:
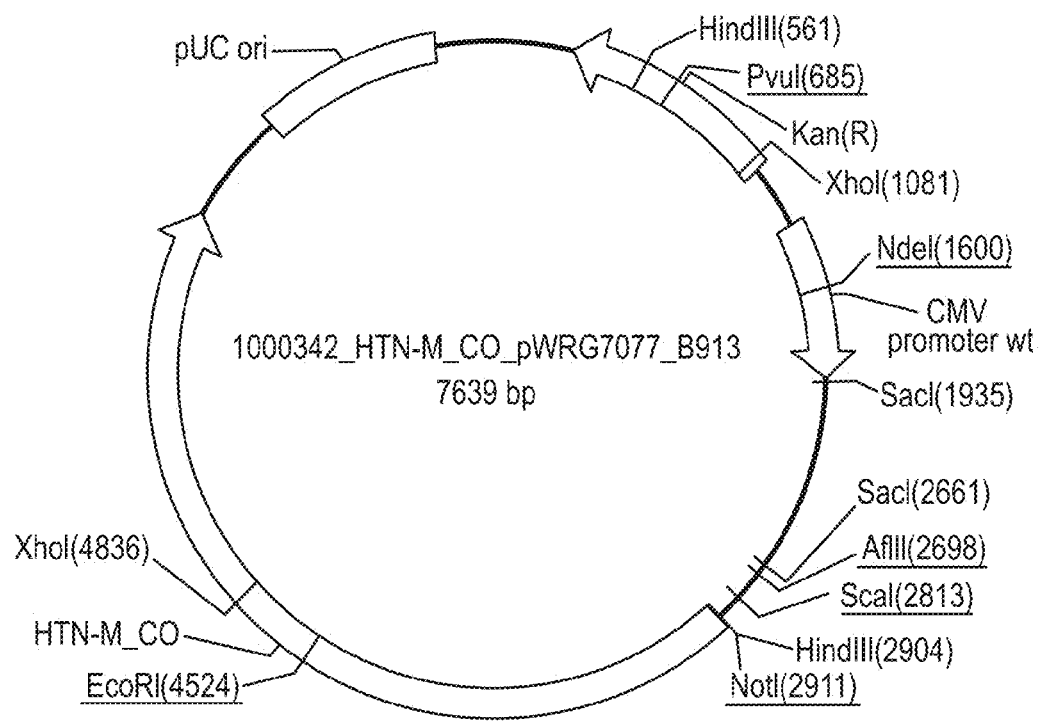
FIG. 6 is a plasmid map of the synthetic gene HTN-M_CO, consisting of 3415 base pairs assembled from synthetic oligonucleotides and/or PCR products into a pWRG7077 plasmid.

The HTNV DNA vaccine expresses the envelope protein genes of HTNV that were adapted to the codon bias of *Homo sapiens* genes. The codon adaption index, which describes how well the codons match the codon usage preference of *homo sapiens*, where 1.0 is perfect, was increased for the HTNV gene from 0.67 to 0.97. In addition, regions of the very high (>80%) or very low (<30%) guanine-cytosine (GC) content were avoided in the genes where possible as either extreme results in poor expression. For the HTNV gene, the average GC content was increased from 40% to 60%, to prolong mRNA half-life. Also, negative cis-acting motifs, such as splice sites, poly(A) signals, TATA-boxes, etc. which may negatively influence expression were eliminated where possible. The optimized HTNV gene open reading frame was then synthesized by Geneart, Inc. (Regensburg, Germany) and inserted between the NotI and BglII restriction sites of plasmid backbone pWRG7077 [30] (to create the DNA vaccine construct that comprise the invention (See FIG. 6). The pWRG7077 plasmid backbone (pWRG7077 (4326 bp) (PowderJect Vaccines, Inc., Madison, Wis.) contains the human cytomegalovirus immediate early (CMV IE) promoter with its associated Intron A, a bovine growth hormone transcription terminator and polyadenylation signal (BGH pA), a pUC19 origin of replication (ori), and a kanamycin resistance marker (KanR) shown in FIG. 6. The complete nucleotide sequence of the final HTNV DNA vaccine construct has been confirmed as shown in SEQ ID No. 1.

Figures 7A, 7B:
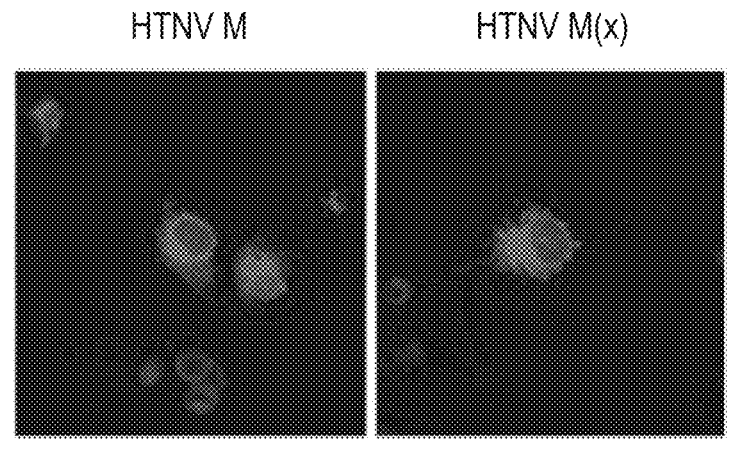
Figure 7C:
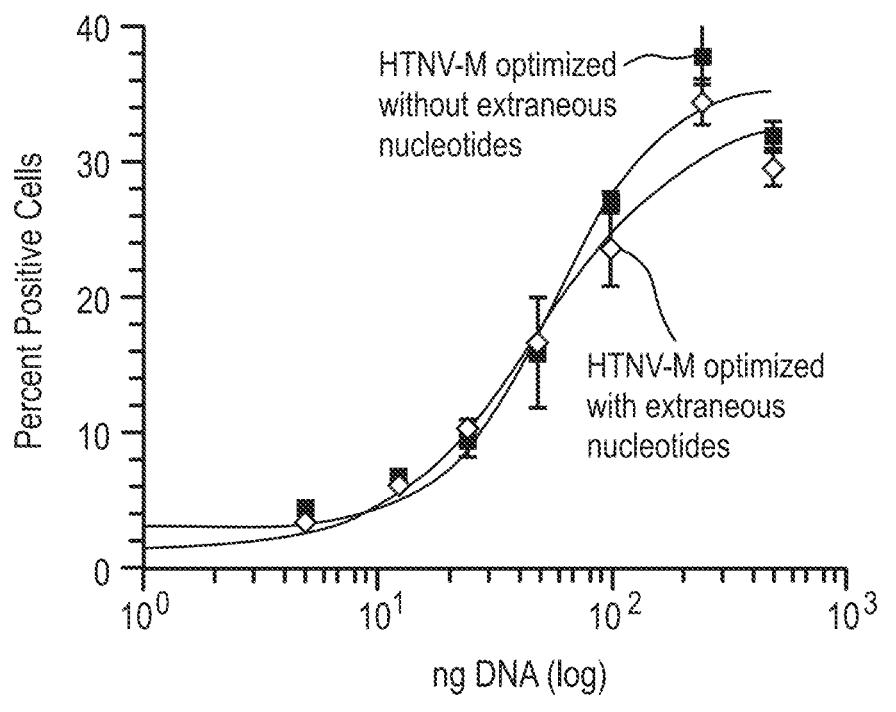

The optimized HTNV DNA vaccine produces HTNV protein that can be recognized in immunofluorescent antibody assays and by flow cytometry when reacted with a monoclonal antibody to a HTNV envelope glycoprotein (FIG. 7A). In addition, the HTNV gene that comprises the invention shows comparable expression in cell cultures to the previously developed, non-optimized HTNV M DNA vaccine, which has non-coding extraneous nucleotides that are required for expression (FIG. 7B). The optimized gene in this invention does not require the extraneous nucleotides for expression, and addition of these nucleotides to the construct does not improve expression. As shown in FIG. 7C, a flow cytometry comparison of the optimized HTNV M that were synthesized with or without the extraneous nucleotides had the same expression profiles. Therefore, the invention is an improvement over the earlier DNA vaccine construct in that it does not require the presence of noncoding nucleotides to produce HTNV proteins.

Figure 7D:
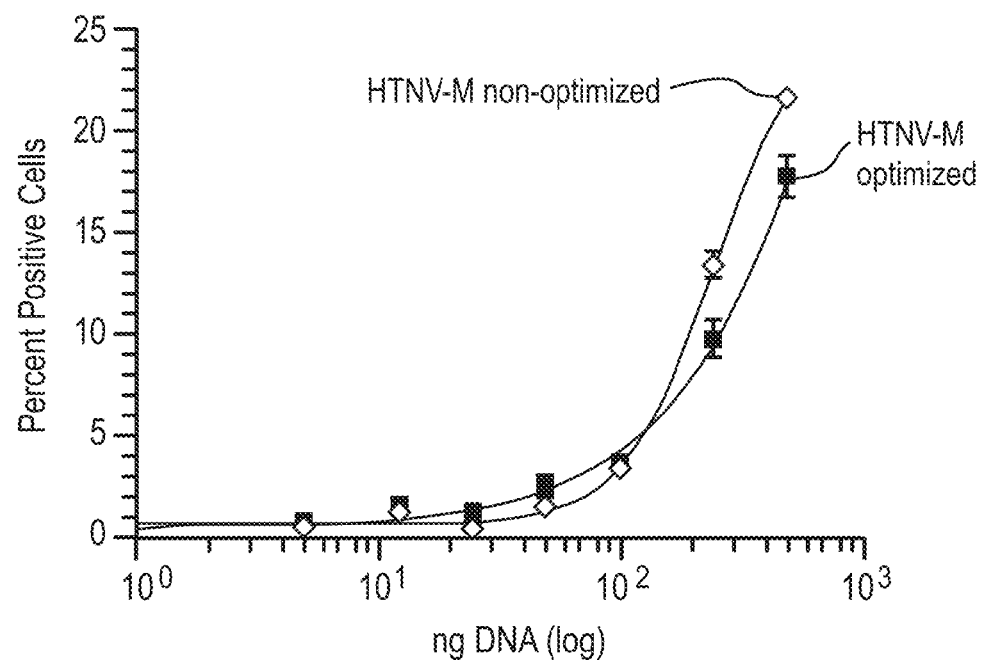

In FIG. 7D, flow cytometry was performed in order to compare expression of the non-optimized (original) HTNV M DNA to the optimized (HTNV_M_CO) DNA. Two curves are shown, which represent independent analysis. The synthetic gene has a similar expression profile as that of the original gene. Conclusions were that the synthetic gene produces HTNV proteins that are recognized by antibodies to authentic HTNV and expression does not require the presence of the extraneous nucleotides that must be present for expression of the original gene.

Figure 8B:
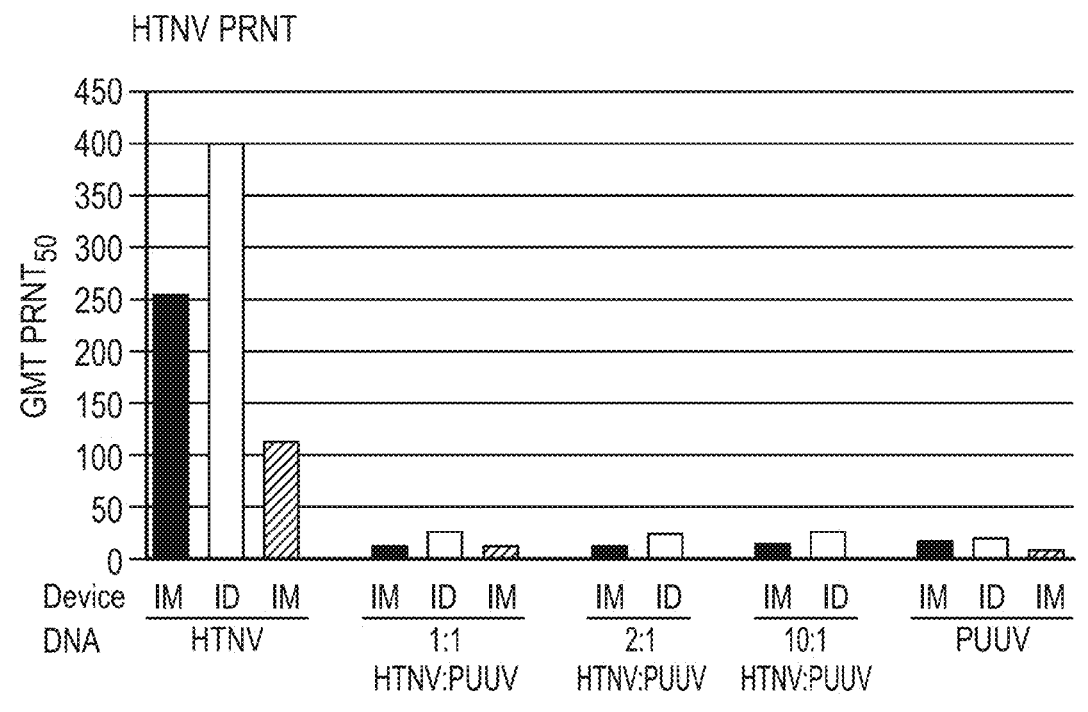

Of primary importance for this invention, the new synthetic DNA vaccine construct solves a major gene-related interference problem, which prevented development of a comprehensive vaccine for HFRS. That is, in order to elicit protective immunity against all four hantaviruses that are able to cause HFRS, it is necessary to vaccinate with both the HTNV DNA vaccine and also with the PUUV DNA vaccine [28, 29]. However, when the native M segment HTNV DNA vaccine was delivered to test animals in combination with the PUUV M segment DNA vaccine, the animals developed antibody responses only to the PUUV component (FIG. 8, and [31]). It was not possible to overcome this interference by increasing the ratio of HTNV to PUUV DNA in the mixture (FIG. 8B).

In FIGS. 8A and 8B, there is shown immunogenicity of HTNV DNA vaccines delivered to hamsters using two types of IM-EP devices or one type of ID-EP device. In FIG. 8A, shown are geometric mean titers (GMT) of neutralizing antibodies to PUUV measured by plaque reduction neutralization test (PRNT) of serum from hamsters vaccinated with optimized PUUV DNA or with a 1:1 mixture of non-optimized HTNV and optimized PUUV DNA. The hamsters develop neutralizing antibodies to PUUV in all groups, indicating that non-optimized HTNV DNA does not interfere with optimized PUUV DNA immunogenicity. In FIG. 8B, there is shown GMT of neutralizing antibodies to HTNV measured by PRNT of serum from hamsters vaccinated with non-optimized HTNV DNA or with 1:1, 2:1 or 10:1 mixtures of non-optimized HTNV and optimized PUUV DNA or with optimized PUUV DNA. Results show that the non-optimized HTNV vaccine elicits neutralizing antibodies to HTNV in hamsters, but that the optimized PUUV vaccine and the mixed vaccines do not, indicate in the PUUV vaccine alone cannot elicit antibody responses to HTNV in hamsters and that mixing the PUUV vaccine with the non-optimized HTNV vaccine results in interference with the immunogenicity of the non-optimized HTNV vaccine. Titers shown are the reciprocal of the dilution of sera required to reduce plaque counts of controls by 50%.

In contrast, using this invention, it is possible to obtain neutralizing antibodies against both HTNV and PUUV in animals that receive the mixed vaccine. In addition, this new optimized HTNV DNA vaccine is at least as effective or more effective than the non-optimized HTNV DNA vaccine at eliciting antibody responses against HTNV when given alone. See FIG. 9. More specifically, in FIG. 9, there is shown the immunogenicity of optimized HTNV of the invention and PUUV DNA vaccines (US 2010/0323024 A1), incorporated herein in its entirety by reference, delivered to hamsters by ID-EP. Geometric mean titers (GMT) of neutralizing antibodies to homologous viruses (first three bars) were measured using sera from hamsters vaccinated with the codon-optimized HTNV DNA vaccine, the non-optimized HTNV DNA vaccine, or the codon-optimized PUUV DNA vaccine. GMT titers to HTNV (fourth bar) or to PUUV (last bar) were measured in sera from hamsters vaccinated with a 1:1 mixture of the optimized HTNV and PUUV M segment optimized DNA vaccines. Titers shown are the reciprocal of the dilution of sera required to reduce plaque counts of controls by 50%.

Delivery:

To accelerate the immune response to the vaccines, the vaccine is delivered using a state-of-the art technology component, electroporation (EP). The DNA is formulated in an excipient approved for human delivery, such as sterile normal saline or other inert substance as a carrier. Both intramuscular (IM) and intradermal (ID) EP devices are available and both have been found to notably enhance the immunogenicity of the HFRS vaccines in animals. ID-EP delivery may be used, which not only capitalizes on the efficient delivery of EP, but also offers the advantages of reduced cost and logistics for mass vaccinations. This bivalent vaccine, in combination with EP delivery accelerates the immune response to the hantaviruses and reduce the number of dosings needed to achieve protective immunity as compared to delivery without EP.

Other delivery methods include jet injection and nanoparticle encapsulation.

To measure the safety of the vaccine in controlled studies under Good Laboratory Practice (GLP) conditions, rabbits are vaccinated with either IM-EP or ID-EP of the optimized vaccine given alone or in combination with the PUUV DNA vaccine. Two manufacturers' EP devices have been tested with the hantavirus DNA vaccines (Ichor and Inovio) in hamsters and both have produced excellent results. IM-EP has been tested more extensively in humans than ID-EP, and is currently the gold standard delivery method for DNA vaccines; however, ID-EP has been found to elicit stronger immune responses than IM-EP for some pathogens because skin is a highly immunologically active organ with numerous circulating antigen presenting cells. In addition to possibly improving immunogenicity with ID-EP, skin vaccination is a desired delivery platform for mass vaccination with biodefense vaccines. Current clinical IM-EP delivery requires loading of DNA vaccine into the delivery device at the time of delivery, whereas the ID-EP platform consists of preloaded disposable cartridges containing the DNA vaccines, which can be administered using a re-useable EP device. The prototype ID-EP device has already been tested in a successfully completed GLP non-clinical safety study in rabbits and humans with another biodefense-related DNA vaccine for Venezuelan equine encephalitis virus.

Together the vaccine and EP delivery platform proposed offers expedient scale-up, long term stability, reduced cold-chain requirements, and mass vaccination applicability.

Safety Study:

A safety study in rabbits was used to obtain approval for testing of the combined non-optimized HTNV and optimized PUUV DNA vaccines in humans. A human study was also recently completed with no serious adverse events related to the vaccines reported. Similarly, a second safety study, also to be performed in rabbits, will be used in support of a pending IM-EP vs ID-EP Phase 1 clinical study with the optimized HTNV DNA vaccine alone and in combination with the optimized PUUV vaccine. The rabbit study characterizes local and/or systemic adverse responses associated with optimized HTNV and/or PUUV vaccine candidates administered using the IM-EP and ID-EP devices. A summary of the repeat dose safety and toxicity study design is shown in Table 1.

TABLE 1

Summary of Repeat Dose Safety/Toxicity Study Design

| Group | Vaccine | Delivery | Dose | Injection # & Volume | Admin. Schedule | N (M/F) | Endpoint |
|---|---|---|---|---|---|---|---|
| 1 | HTNV | IM-EP | 3.0 mg | 1 × 1000 µl | 0, 14, 28, 56 | 20 (10/10) | 5 M/5 F: Day 58<br>5 M/5 F: Day 70 |
| 2 | HTNV | ID-EP | 1.2 mg | 2 × 200 µl | 0, 14, 28, 56 | 20 (10/10) | 5 M/5 F: Day 58<br>5 M/5 F: Day 70 |
| 3 | HTNV + PUUV | IM-EP | 6.0 mg | 1 × 1000 µl | 0, 14, 28, 56 | 20 (10/10) | 5 M/5 F: Day 58<br>5 M/5 F: Day 70 |
| 4 | HTNV + PUUV | ID-EP | 2.4 mg | 2 × 200 µl | 0, 14, 28, 56 | 20 (10/10) | 5 M/5 F: Day 58<br>5 M/5 F: Day 70 |
| 5 | PUUV | ID-EP | 1.2 mg | 2 × 200 µl | 0, 14, 28, 56 | 20 (10/10) | 5 M/5 F: Day 58<br>5 M/5 F: Day 70 |
| 6 | Vehicle (carrier) | IM-EP & ID-EP (no EP) | Saline | 1 × 1000 µl (IM)<br>2 × 200 µl (ID) | 0, 14, 28, 56 | 20 (10/10) | 5 M/5 F: Day 58<br>5 M/5 F: Day 70 |

The invention uses cGMP manufacturing for both the safety study in rabbits and the pending clinical study. The cGMP manufacturing is conducted at a contract research organization and includes extensive release testing for potency, purity and stability, prior to use in the Phase 1 clinical trial.

Clinical Trial

To assess the safety of the optimized HTNV and PUUV DNA vaccines, 6 groups of 10 subjects each for a total of 60 subjects and 12 alternate subjects are vaccinated with the optimized HTNV vaccine, the optimized PUUV vaccine or a mixture of both vaccines. Subjects in one group receive the HTNV DNA vaccine candidate administered using the TDS-IM-EP delivery device (3.0 mg dose). Two other groups receive either the HTNV or PUUV DNA vaccines delivered by the ID-EP device (0.6 mg dose), and two groups receive the HTNV-PUUV mixed vaccine candidate administered using the IM-EP (6.0 mg total dose) or ID-EP device (1.2 mg total dose). Ten subjects receive a placebo control (5 by ID-EP, 5 by IM-EP). Note that differences in dose levels for the two routes of administration are due to the difference in volume of injection that will be administered by the respective routes (0.2 ml ID versus 1.0 ml IM).

Example 1: (Non-Optimized HTNV Study, in Which HTNV and PUUV Vaccines are Delivered as Separate Administrations)

Candidate DNA vaccines for hemorrhagic fever with renal syndrome expressing the envelope glycoprotein genes of Hantaan (HTNV) or Puumala (PUUV) viruses were evaluated in an open-label, single-center Phase 1 study consisting of three vaccination groups of nine volunteers. The volunteers were vaccinated by particle-mediated epidermal delivery (PMED) three times at four-week intervals with the HTNV DNA vaccine, the PUUV DNA vaccine or both vaccines. At each dosing, the volunteers received 8 µg DNA/4 mg gold. There were no study-related serious adverse events, and all injection site pain was graded as mild. The most commonly reported systemic adverse events were fatigue, headache, malaise, myalgia, and lymphadenopathy. Blood samples were collected on days 0, 28, 56, 84, 140, and 180, and assayed for the presence of neutralizing antibodies. In the single vaccine groups, neutralizing antibodies to HTNV or PUUV were detected in 30% or 44% of individuals, respectively. In the combined vaccine group, 56% of the volunteers developed neutralizing antibodies to one or both viruses. These results demonstrate that the HTNV and PUUV DNA vaccines are safe and can be immunogenic in humans when delivered as separate administrations by PMED (FIGS. 1, 2A, 2B, 3, 4A, 4B, 5).

As shown in FIG. 3, neutralizing antibodies to PUUV detected in all samples of two subjects, indicating that there was a pre-existing exposure to a hantavirus prior to the start of this study; But when the person with the pre-existing antibodies to PUUV was vaccinated with the non-optimized HTNV vaccine, they had minimal response to the non-optimized HTNV vaccine, providing evidence that there is no boost in antibody response (i.e. interference in developing HTNV antibodies) even in individuals that have pre-existing antibodies to PUUV;

Example 2: (Non-Optimized HTNV Study, in Which the HTNV and PUUV DNA Vaccines are Given as a Mixture, Resulting in Interference)

In this study, vaccines were delivered using Ichor medical System's IM-EP device. The study included 3 randomized groups of 9 subjects, each of whom received three vaccinations at days 0, 28, and 56 with 2 mg of DNA/1 mL of the non-optimized HTNV vaccine, the optimized PUUV vaccine, or a mixture of both vaccines. Three vaccinations were given four weeks apart. No serious adverse events related to the vaccine were observed. Analysis of blinded serum samples indicated that neutralizing antibodies were elicited against both HTNV and PUUV, but that in volunteers receiving both vaccines, interference was observed, with only three subjects developing neutralizing antibodies to HTNV (FIG. 12C) as compared to seven developing neutralizing antibodies to PUUV (FIG. 12D).

Example 3: (Non-Optimized HTNV DNA Preclinical Safety Study in Rabbits Showing that Mixed HTNV and PUUV DNA Vaccines Result in Reduced Response to HTNV in Rabbits, i.e., Interference)

Figure 11A:
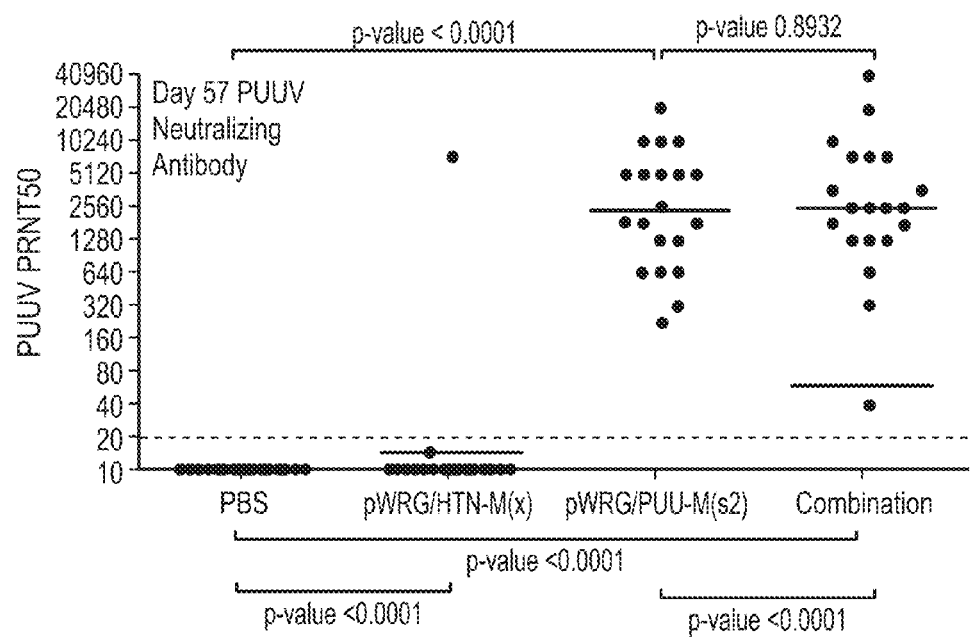
FIG. 11A is a graph showing neutralizing antibodies to PUUV of individual rabbits vaccinated by intramuscular electroporation with non-optimized HTNV DNA vaccine (pWRG/HTN-M(x) as compared to the PUUV DNA vaccine (pWRG/PUU-M(s2) or a mixture of the two vaccines (Combination) showing equivalent neutralizing antibody titers to PUUV.
Figure 11B:
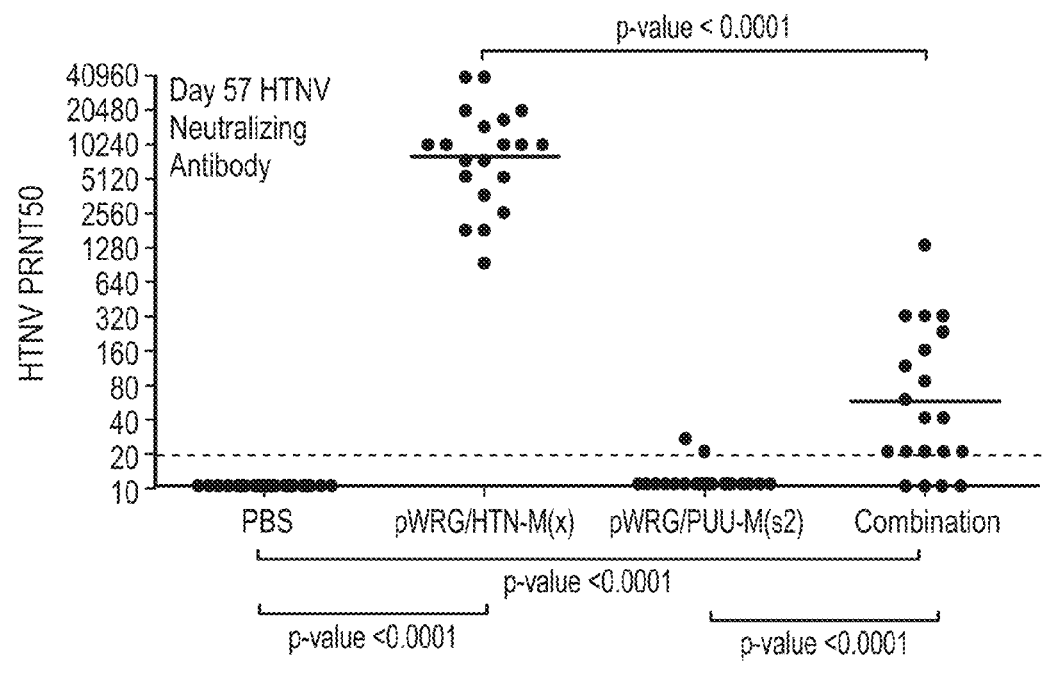

In FIGS. 11A and 11B, results from a GLP safety study of non-optimized HTNV DNA vaccine and optimized PUUV DNA are shown. The vaccine delivered to rabbits by electroporation was performed. Rabbits were vaccinated three times by IM-EP with individual or mixed vaccines (1 mg each) and neutralizing antibodies were measured. Control rabbits were vaccinated with phosphate buffered saline (PBS) using IM-EP for delivery. The data show that equivalent neutralizing antibody titers to PUUV were elicited when the PUUV vaccine, pWRG/PUUM(s2), is given alone or mixed with the non-optimized HTNV DNA vaccine, pWRG/HTNM(x) (FIG. 11A); however, greatly reduced titers to HTNV were observed with the mixed vaccines as compared to those obtained with the HTNV DNA vaccine alone (FIG. 1B).

Example 4: (Optimized HTNV Study in Hamsters Showing that Interference has Been Overcome Using the Inventive Optimized HTNV DNA Vaccine)

Figure 9:
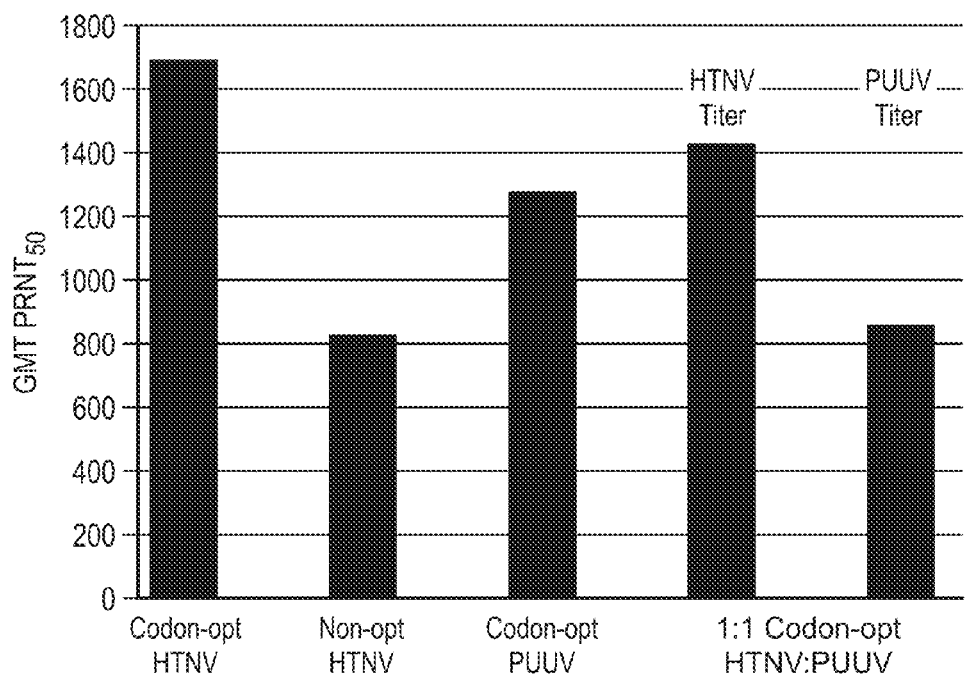
Figure 10:
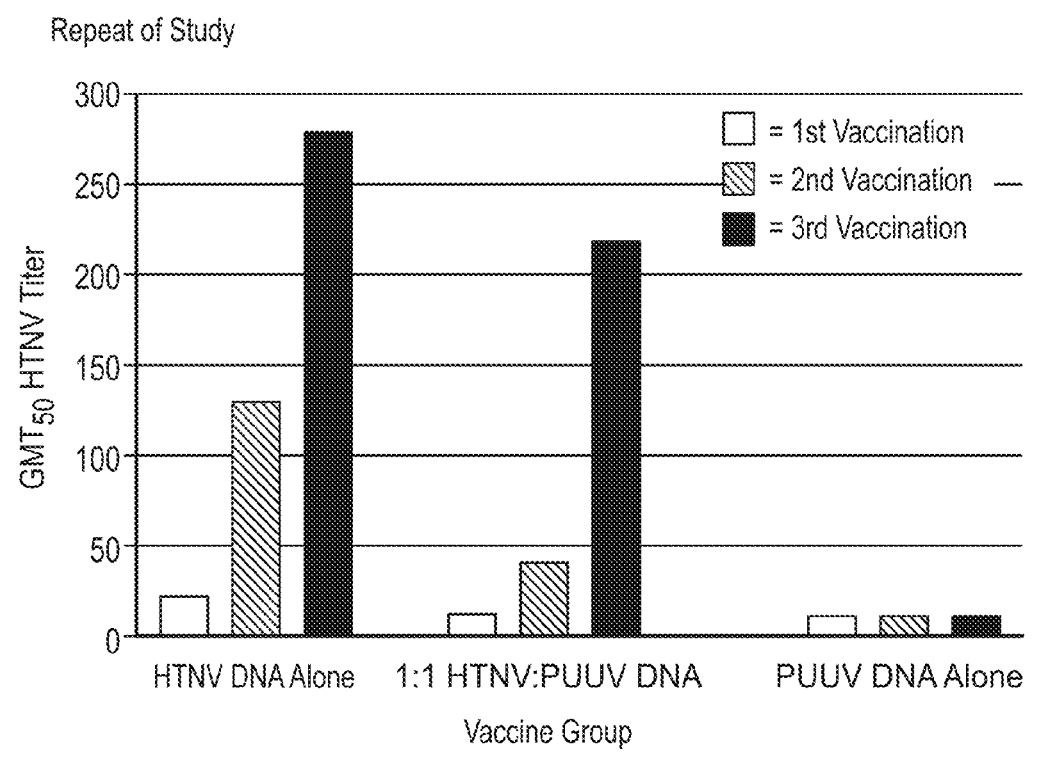

FIG. 9 and FIG. 10 demonstrate the immunogenicity of the inventive optimized HTNV DNA vaccine when mixed 1:1 with PUUV DNA vaccine (US 2010/0323024A1) delivered to hamsters by IM-EP in two separate studies. The hamsters were vaccinated three times at 3-4 week intervals by IM-EP with 100 μg of the individual DNAs or with a 1:1 mixture the optimized HTNV and PUUV DNAs (50 μg of each). Geometric mean antibody titers ($GMT_{50}$) for each group of eight hamsters are shown as the reciprocal of the dilution of sera required to reduce plaque counts of controls by 50%. As expected, because half as much of the optimized HTNV DNA was given in the mixture as compared to in those receiving only the optimized HTNV DNA vaccine, the antibody response to HTNV was slightly reduced. Following injection of HTNV into the vaccinated hamsters, it was determined that none of the hamsters vaccinated with the mixed vaccines showed evidence of infection with HTNV (as determined by measuring antibodies to the N protein, which is not part of the vaccine, data not shown). Consequently, the mixed vaccines containing the inventive optimized HTNV DNA vaccine can elicit neutralizing antibodies against HTNV and also protect from infection by HTNV. Moreover, there was no detectable interference observed when the inventive HTNV DNA vaccine was mixed with the PUUV DNA vaccine.

Example 5: (Non-Optimized HTNV DNA Vaccine Phase 1 Clinical Study Using IM-EP Delivery, Showing that Mixed HTNV and PUUV DNA Vaccines Result in Reduced Response to HTNV, i.e., Interference)

FIG. 12 A-D show neutralizing antibody responses of volunteers vaccinated by IM-EP with the individual or mixed non-optimized HTNV and optimized-PUUV DNA vaccines. Seven of eleven volunteers that were vaccinated with the non-optimized HTNV DNA vaccine developed neutralizing antibodies to HTNV. Six of eight volunteers vaccinated with optimized PUUV vaccine developed neutralizing antibodies to PUUV. Three of nine volunteers vaccinated with the combination vaccine developed antibodies to both HTNV and PUUV. However four additional volunteers had antibodies only to PUUV but no additional volunteers had antibodies only to HTNV. Interference, while not complete, is still a problem. These results are in line with the results in Example 2.

Preparation of Optimized DNA Vaccines

The optimized HTNV DNA vaccine was constructed by cloning cDNA representing the optimized HTNV M segment open reading frame, which encodes Gn and Gc, into the NotI and BglII-restriction sites of pWRG7077 [14] as described previously [8]. The PUUV DNA vaccine was previously constructed similarly, using cDNA that was engineered as a consensus sequence of several PUUV strains, and codon-optimized (GeneArt) [15] and (US 2010/0323024A1). The HTNV and PUUV DNA vaccines were produced under current Good Manufacturing Practices (cGMP) by Althea Technologies, Inc. (San Diego, Calif.). A summary of the manufacturing and testing processes that Althea was contracted to perform is as follows:

Optimized HTNV DNA vaccine plasmid is manufactured under cGMP specification, to include (a) Establishment and Characterization of a Manufacturer's Master Cell Bank (MCB) (b) Process Optimization & Non-GMP Production of a HTNV plasmid DNA vaccine lot, (c) cGMP Production and Characterization of a bulk HTNV Plasmid DNA (2.6 g) (d) Packaging and Shipment of Cell Banks (2 SHIPMENTS), (e) 6 months Bulk Drug Product Storage. Deliverables requested from Althea are (1) a Master cell bank for HTNV, (2) a pilot lot of HTNV DNA plasmid; (3) one cGMP lot of bulk DNA plasmid stored in IPA (2.6 g); and (4) all documents (e.g., batch records, data records and reports, CoAs, BMF letter of cross reference) as required for submission to FDA.

The following specific tasks are performed by Althea for manufacture of a bulk DNA vaccine plasmid for HTNV.

Example 6: (Optimized HTNV Vaccine)

Figure 13:
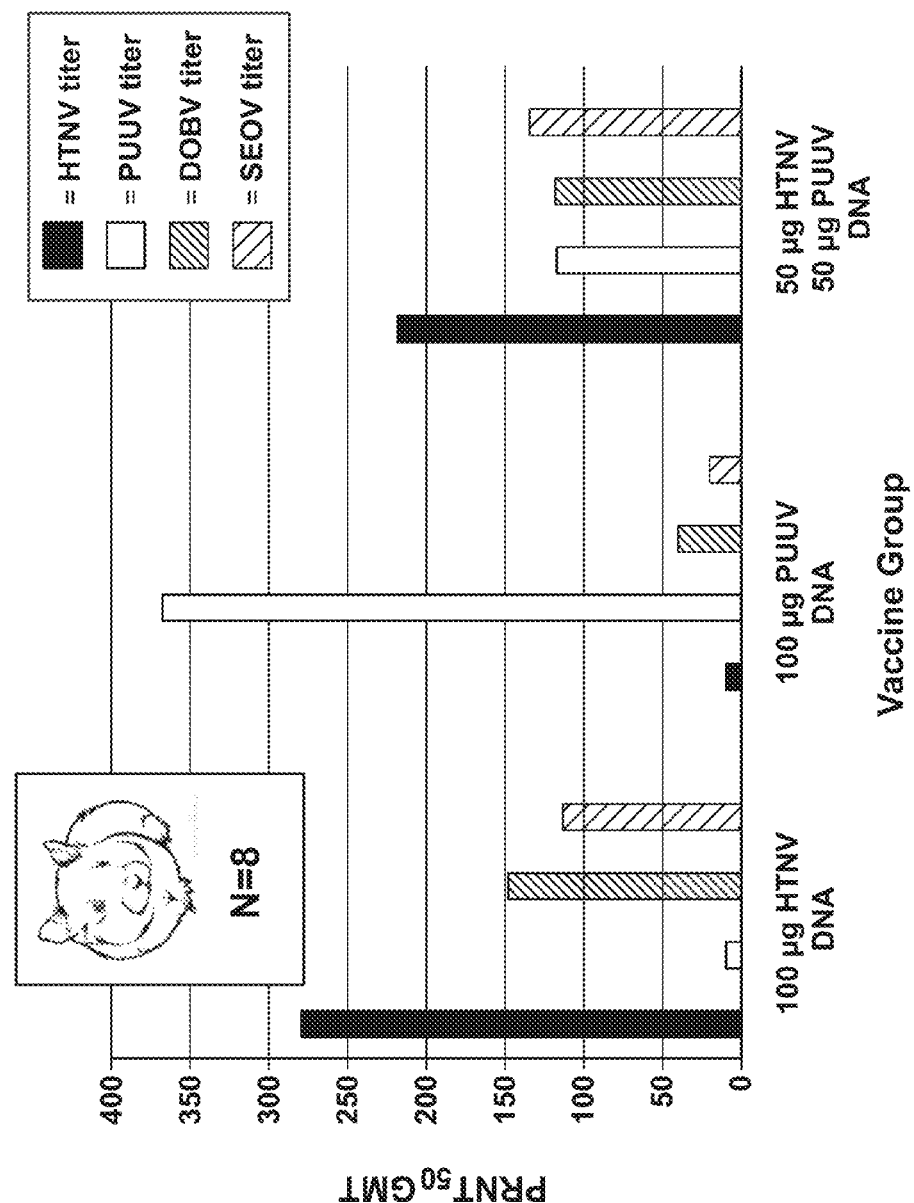
FIG. 13 is a graph showing a hamster study showing the results of geometric mean titers of neutralizing antibodies to each of four hantaviruses known to cause hemorrhagic fever with renal syndrome in hamsters vaccinated with the optimized HTNV DNA vaccine alone, the optimized PUUV DNA vaccine alone or a mixture of the optimized HTNV and PUUV DNA vaccines indicating that the optimized HTNV vaccine induces antibodies to HTNV, SEOV, and DOBV, but not to PUUV); the optimized PUUV vaccine elicits antibodies only to PUUV, but that the mixture of the optimized HTNV and PUUV vaccines induces neutralizing antibodies to all four of the hantaviruses.
Figure 15A:
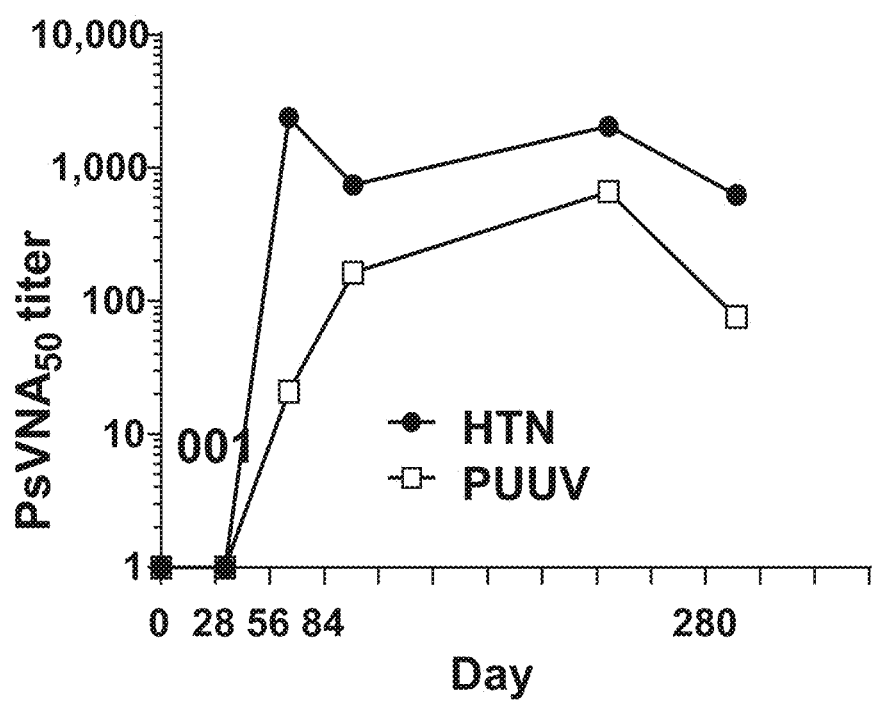
FIG. 15A is a graph showing showing pseudovirion neutralization titers from the clinical study in individual 001 responding to both of the optimized vaccines delivered as a mixture by IM-EPe.
Figure 15B:
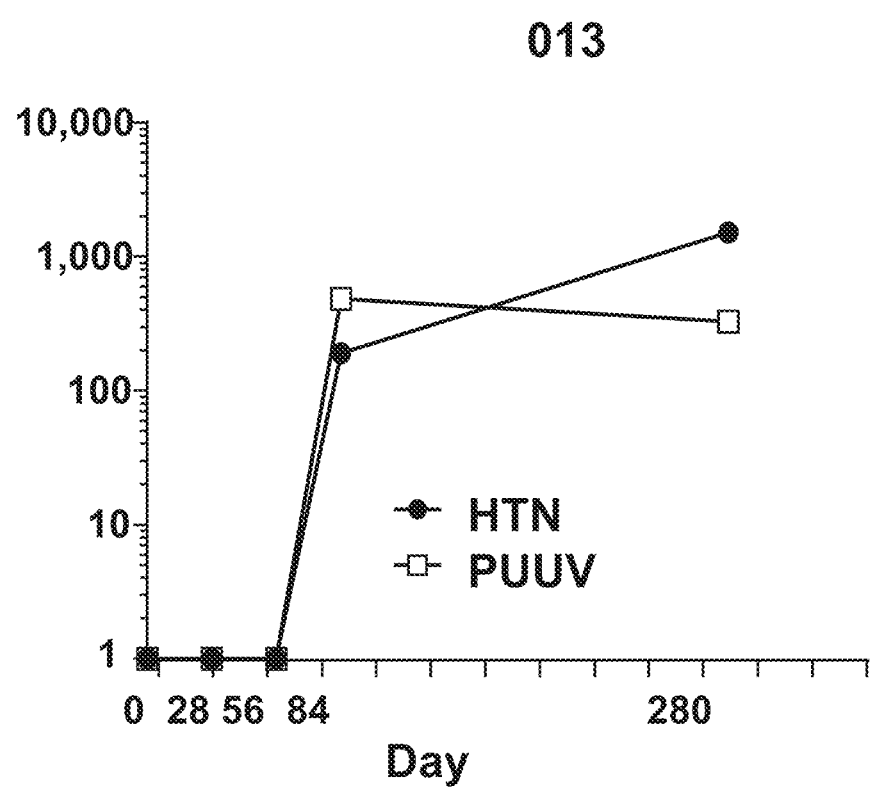
FIG. 15B is a graph showing showing pseudovirion neutralization titers in individual 013 responding to both vaccines.
Figure 15C:
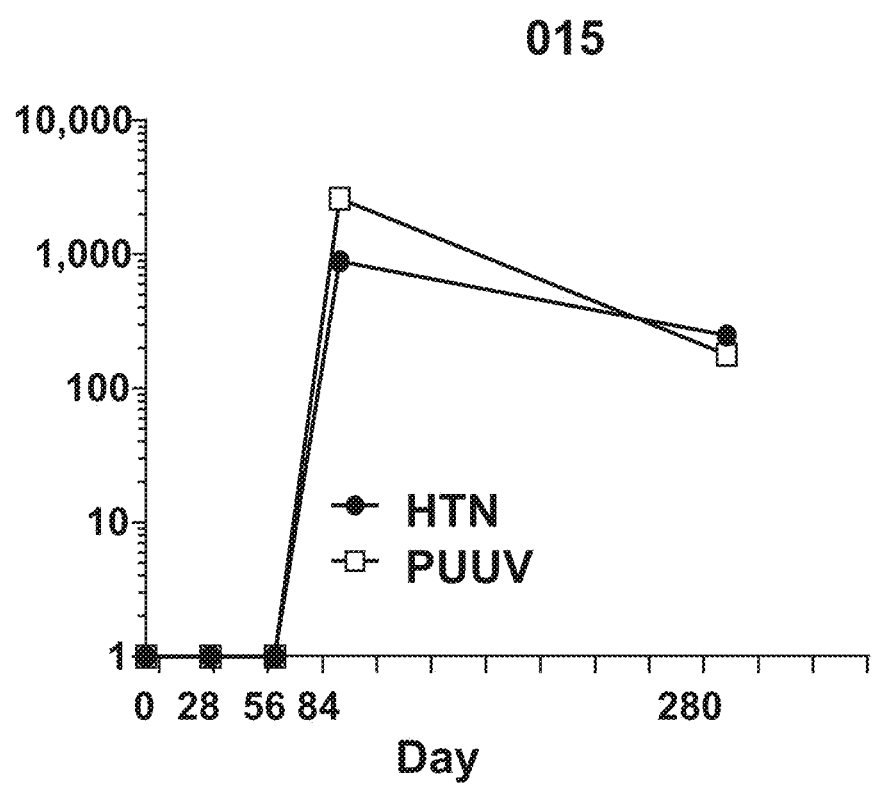
FIG. 15C is a graph showing showing pseudovirion neutralization titers in individual 015 responding to both vaccines.
Figure 15D:
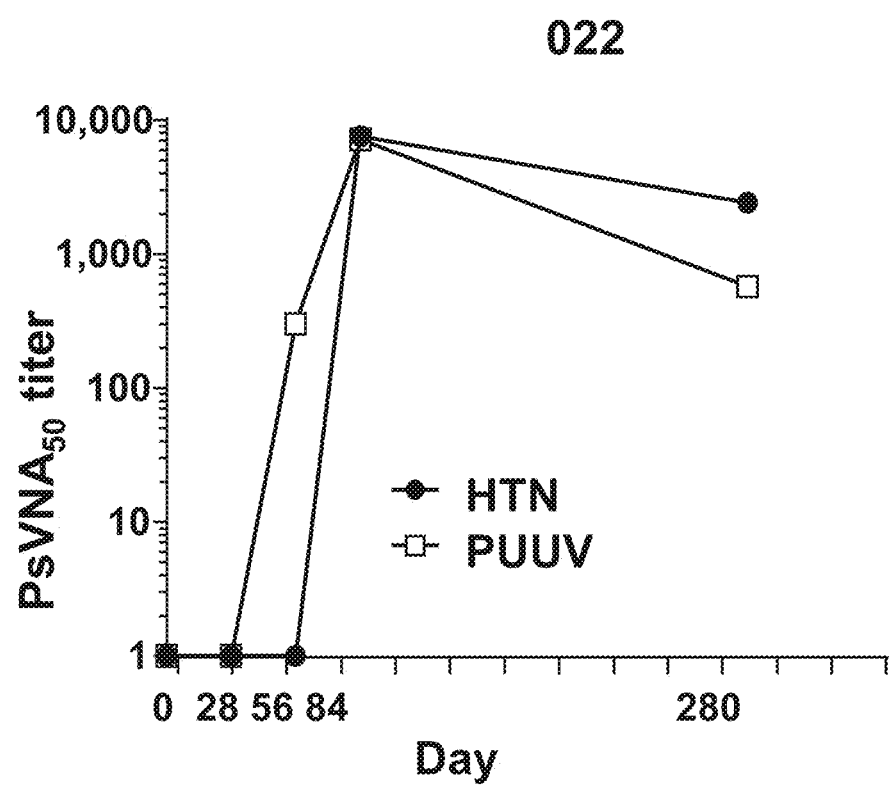
FIG. 15D is a graph showing showing pseudovirion neutralization titers in individual 022 responding to both vaccines.
Figure 15E:
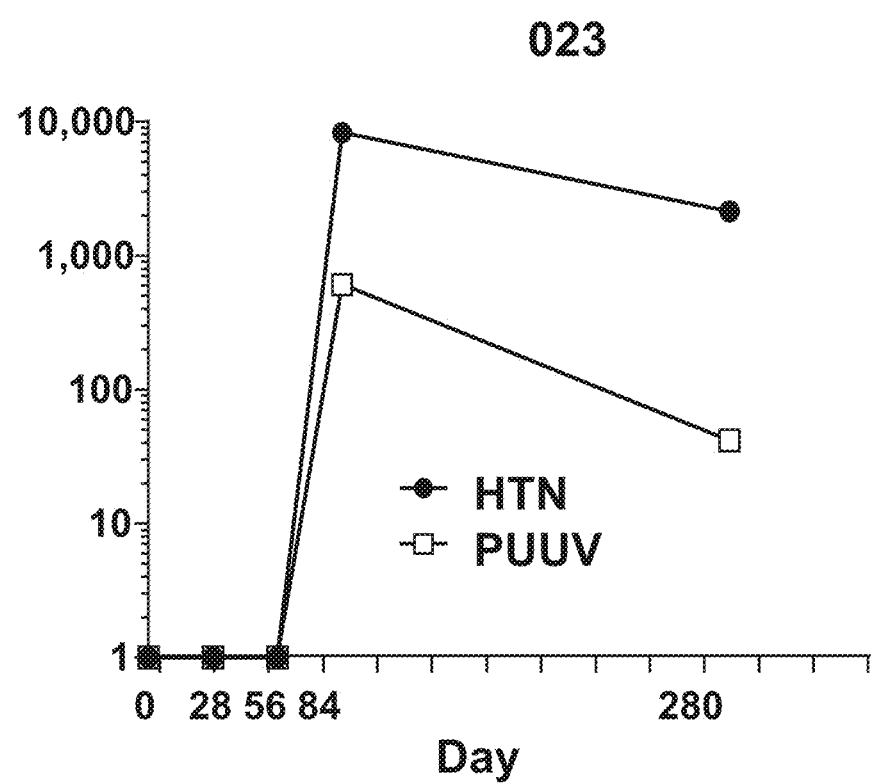
FIG. 15E is a graph showing showing pseudovirion neutralization titers in individual 023 responding to both vaccines.
Figure 15F:
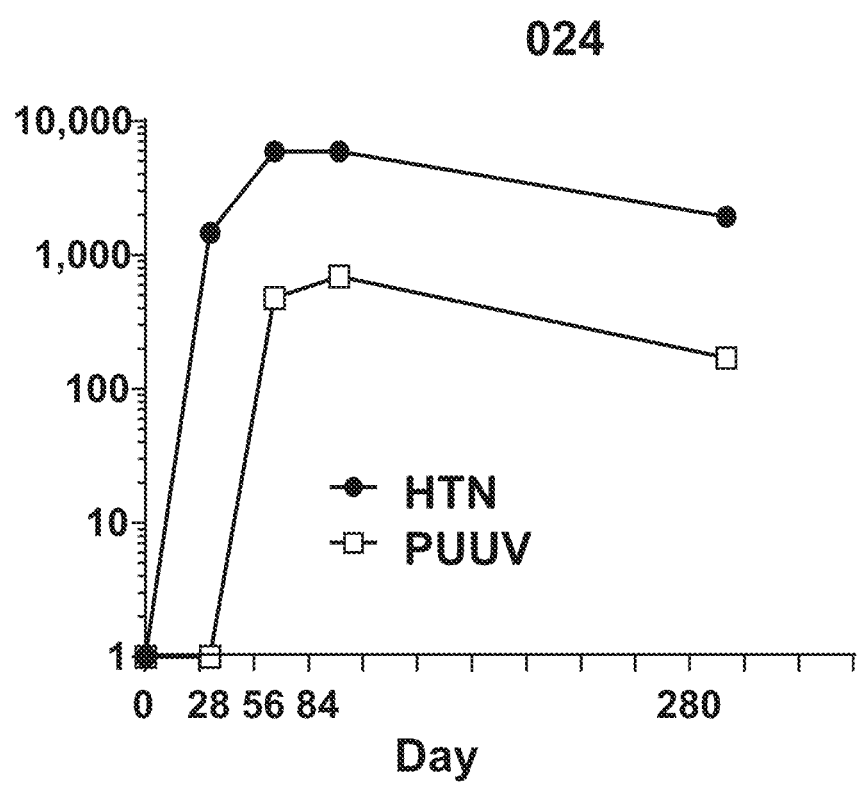
FIG. 15F is a graph showing showing pseudovirion neutralization titers in individual 024 responding to both vaccines.

As shown in FIG. 13, gene modifications to overcome interference were made. As previously performed for the PUUV plasmid, the codons of the HTNV plasmid were modified to the bias of homo sapiens genes, and known motifs that reduce expression were removed. Hamsters vaccinated with the optimized vaccine of the invention by ID-EP three times at 3-week intervals developed neutralizing antibodies to all four HFRS-causing hantaviruses.

Example 7

FIG. 14 shows a study design for 120 people that receive a mixed optimized vaccine. Two different doses are given (2 mg vs 1 mg) and 2 different schedules with each individual receiving an optional 6-month boost.

FIGS. 15a-15f show examples of pseudovirion neutralization titers in various individuals from the study of FIG. 14 responding to both optimized HTNV and PUUV vaccines. Vesicular stomatitis viruses were pseudo typed with optimized HTNV or PUUV glycoproteins and used to assess neutralizing antibody responses of Phase 2a vaccine recipients at indicated days post vaccination. The individuals of FIGS. 15a-15f are also represented in FIG. 16.

Example 8

Figure 16:
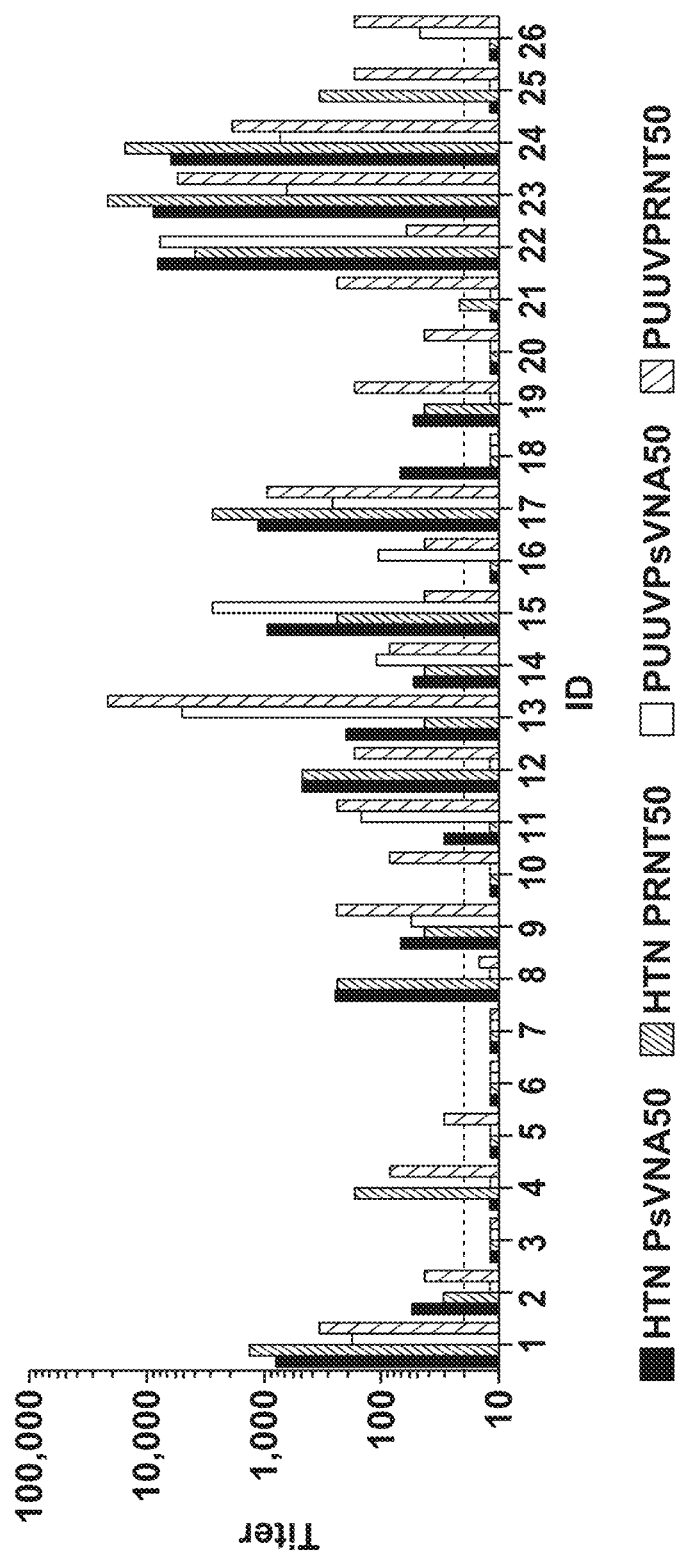
FIG. 16 is a graph showing neutralizing antibody responses in 26 vaccine recipients four weeks after the third vaccination with the mixed optimized HTNV and PUUV DNA vaccine by IM-EP, indicating high antibody responses to both viruses in some individuals.

FIG. 16 also shows results from the study design of FIG. 14. FIG. 16 shows neutralizing antibody responses detected in sera of the first 26 vaccine recipients four weeks after the third vaccination with optimized HTNV and PUUV DNA vaccines by IM-EP. As samples are blinded until completion of this study, it is not possible to assess dose or route factors with these samples. The neutralizing antibody titers were measured using a traditional plaque reduction neutralization test (PRNT) or a vesicular stomatitis virus pseudo typed with the glycoproteins of optimized HTNV or PUUV (Ps-VNA). The bars show each person's neutralizing antibodies to optimized Hantaan or Puumala viruses as measured by the two different tests. The first test uses authentic HTNV (plaque reduction neutralization test) and the second test uses a nonpathogenic virus (VSV) that is coated with HTN proteins (pseudovirion neutralization assay). This second assay can be completed quickly and at BSL2 rather than BSL3 conditions.

Summary:

Phase 1 study results show that DNA vaccines expressing the envelope glycoprotein genes of HTNV and PUUV are safe and immunogenic in humans when delived by IM-EP.

Animal studies suggest that immune interference between the HTNV and PUUV plasmids can be resolved using gene-optimized plasmids. Dose and schedule studies are in progress using the optimized plasmids.

Figure 17:
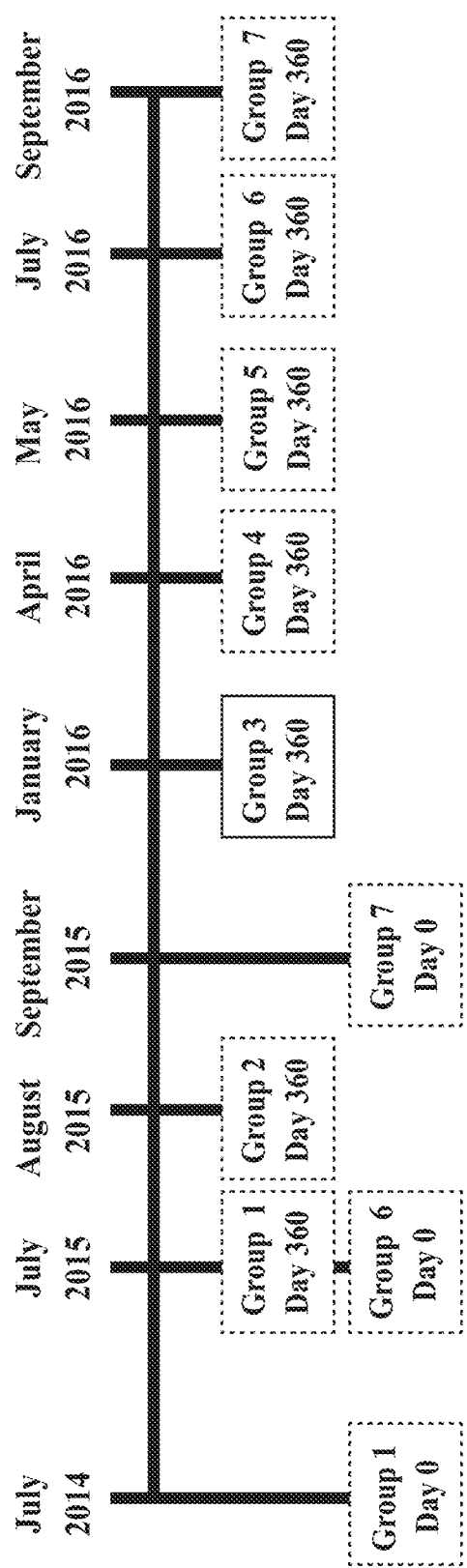
FIG. 17 is a Timeline graph of the Phase 2a study.

Preliminary (blinded) analysis of sera from a subset of Phase 2a time points (FIG. 17) shows that in the first 26 vaccinees, the overall seroconversion rate is 92% with 81% positive for optimized HTNV and 88% positive for PUUV at one or more time points.

Establishment of Master Cell Bank (MCB)
Includes:
  Preparation of MCB batch record
  Transformation
  Selection, genetic stability
  Growth
  Dispensing/freezing (no less than 200 vials)
Characterization of MCB
Includes:
  Completion of MCB testing outlined in Attachment 1
  QA review of associated testing
  Generation of C of A
Non-GMP Production/Process Optimization
Includes:
  Evaluation of plasmid in Althea's fermentation and purification processes
  Non-GMP plasmid will be provided to USAMRMC for research use only
  Appearance, size, and identity of plasmid by restriction analysis using two common enzymes
  Purity by gel electrophoresis
  A260/280 (1.7/2.0)
  Endotoxin by LAL
  An optimization study must be completed prior to GMP Production
cGMP Production and Characterization of Plasmid DNA (2.6 g)
Includes:
  Establishment of specifications
  Preparation of customized cGMP Manufacturing Batch Records
  Optimization of fermentation conditions
  Fermentation
  Development of large scale purification process
  Cell lysis
  Downstream processing and separation
  Column purification
  Preparation of standard bulk
  In-process testing
Shipping
Packaging and Shipment of Cell Banks (2SHIPMENTS)
  Includes the management and preparation of the cell banks
  Includes verification of shipment products from Althea to a USAMRMC specified destination
  Includes temperature controlled shipping containers with temperature loggers
  Preparation of all required shipping documentation
  Shipping on Dry Ice
Bulk Drug Product Storage (6 Months)
  Includes temperature monitored storage of Bulk Drug Product.

```
pWRG7077HTN-M-CO
DNA of M segment and plasmid together
                                            SEQ ID NO. 1
GGGGGGGGGGGGCGCTGAGGTCTGCCTCGTGAAGAAGGTGTTGCTGACTC

ATACCAGGCCTGAATCGCCCCATCATCCAGCCAGAAAGTGAGGGAGCCAC

GGTTGATGAGAGCTTTGTTGTAGGTGGACCAGTTGGTGATTTTGAACTTT

TGCTTTGCCACGGAACGGTCTGCGTTGTCGGGAAGATGCGTGATCTGATC

CTTCAACTCAGCAAAAGTTCGATTTATTCAACAAAGCCGCCGTCCCGTCA

AGTCAGCGTAATGCTCTGCCAGTGTTACAACCAATTAACCAATTCTGATT

AGAAAAACTCATCGAGCATCAAATGAAACTGCAATTTATTCATATCAGGA

TTATCAATACCATATTTTTGAAAAAGCCGTTTCTGTAATGAAGGAGAAAA

CTCACCGAGGCAGTTCCATAGGATGGCAAGATCCTGGTATCGGTCTGCGA

TTCCGACTCGTCCAACATCAATACAACCTATTAATTTCCCCTCGTCAAAA

ATAAGGTTATCAAGTGAGAAATCACCATGAGTGACGACTGAATCCGGTGA

GAATGGCAAAAGCTTATGCATTTCTTTCCAGACTTGTTCAACAGGCCAGC

CATTACGCTCGTCATCAAAATCACTCGCATCAACCAAACCGTTATTCATT

CGTGATTGCGCCTGAGCGAGACGAAATACGCGATCGCTGTTAAAAGGACA

ATTACAAACAGGAATCGAATGCAACCGGCGCAGGAACACTGCCAGCGCAT

CAACAATATTTTCACCTGAATCAGGATATTCTTCTAATACCTGGAATGCT

GTTTTCCCGGGGATCGCAGTGGTGAGTAACCATGCATCATCAGGAGTACG

GATAAAATGCTTGATGGTCGGAAGAGGCATAAATTCCGTCAGCCAGTTTA

GTCTGACCATCTCATCTGTAACATCATTGGCAACGCTACCTTTGCCATGT

TTCAGAAACAACTCTGGCGCATCGGGCTTCCCATACAATCGATAGATTGT

CGCACCTGATTGCCCGACATTATCGCGAGCCCATTTATACCCATATAAAT

CAGCATCCATGTTGGAATTTAATCGCGGCCTCGAGCAAGACGTTTCCCGT

TGAATATGGCTCATAACACCCCTTGTATTACTGTTTATGTAAGCAGACAG

TTTTATTGTTCATGATGATATATTTTTATCTTGTGCAATGTAACATCAGA

GATTTTGAGACACAACGTGGCTTTCCCCCCCCCCCGGCATGCCTGCAGG

TCGACAATATTGGCTATTGGCCATTGCATACGTTGTATCTATATCATAAT

ATGTACATTTATATTGGCTCATGTCCAATATGACCGCCATGTTGACATTG

ATTATTGACTAGTTATTAATAGTAATCAATTACGGGGTCATTAGTTCATA

GCCCATATATGGAGTTCCGCGTTACATAACTTACGGTAAATGGCCCGCCT

GGCTGACCGCCCAACGACCCCCGCCCATTGACGTCAATAATGACGTATGT

TCCCATAGTAACGCCAATAGGGACTTTCCATTGACGTCAATGGGTGGAGT

ATTTACGGTAAACTGCCCACTTGGCAGTACATCAAGTGTATCATATGCCA

AGTCCGCCCCCTATTGACGTCaATGACGGTAAATGGCCCGCCTGGCATTA

TGCCCAGTACATGACCTTACGGGACTTTCCTACTTGGCAGTACATCTACG
```

-continued

```
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTTACAGGATGGG
GTCCCATTTATTATTTACAAATTCACATATACAACAACGCCGTCCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
CCGAGCCCTGGTCCCATGCCTCCAGCGGCTCATGGTCGCTCGGCAGCTCC
TTGCTCCTAACAGTGGAGGCCAGACTTAGGCACAGCACAATGCCCACCAC
CACCAGTGTGCCGCACAAGGCCGTGGCGGTAGGGTATGTGTCTGAAAATG
AGCTCGGAGATTGGGCTCGCACCGCTGACGCAGATGGAAGACTTAAGGCA
GCGGCAGAAGAAGATGCAGGCAGCTGAGTTGTTGTATTCTGATAAGAGTC
AGAGGTAACTCCCGTTGCGGTGCTGTTAACGGTGGAGGGCAGTGTAGTCT
GAGCAGTACTCGTTGCTGCCGCGCGCCACCAGACATAATAGCTGACAG
ACTAACAGACTGTTCCTTTCCATGGGTCTTTTCTGCAGTCACCGTCCAAG
CTTGCGGCCGCCACCATGGGCATCTGGAAGTGGCTGGTCATGGCTAGCCT
CGTGTGGCCCGTGCTGACCCTGCGGAACGTGTACGACATGAAGATCGAGT
GCCCCCACACCGTGTCCTTCGGCGAGAACAGCGTGATCGGCTACGTGGAA
CTGCCCCCCGTGCCCCTGGCCGATACAGCTCAGATGGTGCCCGAGAGCAG
CTGCAGCATGGACAACCACCAGAGCCTGAACACCATCACCAAGTACACCC
AGGTGTCCTGGCGGGGCAAGGCCGATCAGAGCCAGAGCAGCCAGAACAGC
TTCGAGACAGTGTCTACCGAGGTGGACCTGAAGGGCACCTGTGCCCTGAA
GCACAAGATGGTGGAAGAGAGCTACCGGTCCAGAAAGAGCGTGACCTGCT
ACGACCTGAGCTGCAACAGCACCTACTGCAAGCCCACCCTGTACATGATC
GTGCCCATCCACGCCTGCAACATGATGAAGTCCTGCCTGATCGCCCTGGG
CCCCTACAGAGTGCAGGTCGTGTACGAGCGGAGCTACTGCATGACCGGCG
TGCTGATCGAGGGCAAGTGCTTCGTGCCCGACCAGAGCGTGGTGTCCATC
ATCAAGCACGGCATCTTCGATATCGCCAGCGTGCACATCGTGTGCTTTTT
CGTGGCCGTCAAGGGCAACACCTACAAGATTTTCGAGCAGGTCAAAAAGA
GCTTCGAGAGCACCTGTAACGACACCGAGAACAAGGTGCAGGGCTACTAC
ATCTGCATCGTGGGCGGCAACAGCGCCCCCATCTACGTGCCCACCCTGGA
CGACTTCCGGTCCATGGAAGCCTTCACCGGCATCTTCAGAAGCCCCCACG
```

-continued

```
GCGAGGACCACGACCTGGCCGGCGAGGAAATCGCCAGCTACTCCATCGTG
GGCCCTGCCAACGCCAAGGTGCCACACAGCGCCAGCAGCGACACCCTGTC
CCTGATCGCCTACAGCGGCATCCCCAGCTACAGCAGCCTGAGCATCCTGA
CCAGCAGCACCGAGGCCAAGCACGTGTTCAGCCCTGGCCTGTTCCCCAAG
CTGAACCACACCAACTGCGACAAGAGCGCCATCCCCCTGATCTGGACCGG
CATGATCGACCTGCCCGGCTACTACGAGGCCGTGCACCCTGCACCGTGT
TCTGCGTGCTGTCTGGCCCTGGAGCCAGCTGCGAGGCCTTTTCTGAGGGC
GGCATCTTTAACATCACCAGCCCCATGTGCCTGGTGTCCAAGCAGAACCG
GTTCCGGCTGACCGAGCAGCAGGTCAACTTCGTGTGCCAGCGGGTGGACA
TGGACATCGTGGTGTACTGCAACGGCCAGCGGAAAGTGATCCTGACCAAG
ACCCTCGTGATCGGCCAGTGCATCTACACCATCACAAGCCTGTTCAGCCT
GCTGCCCGGCGTGGCCCACTCTATCGCCGTGGAACTGTGCGTGCCCGGCT
TTCACGGCTGGGCCACAGCTGCCCTGCTGGTCACCTTCTGCTTCGGCTGG
GTGCTGATCCCCGCCATCACCTTCATCATCCTGACCGTGCTGAAGTTTAT
CGCCAACATCTTCCACACCAGCAACCAGGAAAACCGGCTCAAGTCCGTGC
TGCGGAAGATCAAAGAGGAATTCGAAAAGACCAAGGGCAGCATGGTCTGC
GACGTGTGCAAATACGAGTGCGAGACATACAAAGAGCTGAAGGCCCACGG
CGTGTCCTGCCCTCAGAGCCAGTGCCCCTACTGCTTCACCCACTGCGAGC
CTACCGAGGCCGCCTTCCAGGCCCACTACAAAGTGTGCCAGGTCACACAC
CGGTTCAGGGACGACCTGAAGAAAACCGTGACCCCCCAGAACTTCACCCC
CGGCTGCTACCGGACCCTGAACCTGTTCCGGTACAAGAGCCGGTGCTACA
TCTTTACCATGTGGATCTTTCTGCTGGTGCTCGAGTCCATCCTGTGGGCC
GCCAGCGCCAGCGAAACCCCTCTGACCCCCGTGTGGAACGACAACGCCCA
TGGCGTGGGCTCTGTGCCCATGCACACCGACCTGGAACTGGACTTCAGCC
TGACCAGCTCCAGCAAGTACACCTACCGGCGGAAGCTGACCAACCCCCTG
GAAGAGGCCCAGAGCATCGACCTGCACATCGAGATCGAGGAACAGACCAT
CGGAGTCGATGTCCACGCCCTGGGACATTGGTTCGACGGACGGCTGAACC
TGAAAACCAGCTTCCACTGCTACGGCGCCTGCACTAAGTACGAGTACCCC
TGGCACACCGCCAAGTGCCACTACGAGCGGGACTACCAGTACGAGACAAG
CTGGGGCTGTAACCCCAGCGACTGTCCAGGCGTGGGCACCGGCTGTACAG
CTTGTGGCCTGTACCTGGACCAGCTGAAGCCCGTGGGCTCCGCCTACAAG
ATCATCACCATCCGGTACAGCAGACGCGTGTGCGTGCAGTTCGGCGAAGA
GAACCTGTGCAAGATCATCGACATGAACGACTGCTTCGTGTCCCGGCACG
TGAAAGTGTGCATCATCGGCACCGTGTCCAAGTTCAGCCAGGGCGATACC
CTGCTGTTCTTCGGCCCTCTGGAAGGCGGCGGACTGATCTTCAAGCACTG
GTGCACAAGCACCTGTCAGTTTGGCGACCCCGGCGACATCATGAGCCCCA
GAGACAAGGGCTTCCTGTGCCCCGAGTTCCCCGGCAGCTTCCGGAAGAAG
TGCAACTTCGCCACCACCCCATCTGCGAGTACGACGGCAACATGGTGTC
CGGCTACAAGAAAGTGATGGCCACCATCGACAGCTTCCAGAGCTTCAACA
CCTCCACCATGCACTTCACCGACGAGCGGATCGAGTGGAAGGACCCCGAC
GGCATGCTGCGGGACCACATCAACATCCTGGTCACCAAGGACATCGACTT
```

-continued

CGACAACCTGGGCGAGAACCCCTGCAAGATCGGCCTGCAGACCTCCAGCA
TCGAGGGCGCTTGGGGCAGCGGCGTGGGCTTTACCCTGACCTGTCTGGTG
TCCCTGACCGAGTGCCCCACCTTCCTGACCTCCATCAAGGCCTGCGACAA
GGCCATCTGTTACGGCGCCGAGTCCGTGACCCTGACAAGAGGCCAGAACA
CCGTGAAGGTGTCCGGCAAAGGCGGCCACAGCGGCAGCACCTTCAGATGC
TGCCACGGGGAGGACTGCAGCCAGATCGGACTGCATGCCGCAGCACCCCA
CCTGGACAAAGTGAACGGCATCAGCGAGATCGAGAACTCCAAGGTGTACG
ACGATGGCGCCCCTCAGTGCGGCATCAAGTGTTGGTTCGTGAAGTCCGGC
GAGTGGATCAGCGGCATCTTCTCCGGCAACTGGATCGTGCTGATTGTGCT
GTGCGTGTTCCTGCTGTTTAGCCTGGTGCTGCTGAGCATTCTGTGTCCCG
TGCGCAAGCACAAGAAAAGCTGATGAAGATCTACGTATGATCAGCCTCGA
CTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGA
GGAAATTGCATCGCATTGTCTGAGTAGGTGTCATTCTATTCTGGGGGGTG
GGGTGGGGCAGGACAGCAAGGGGGAGGATTGGGAAGACAATAGCAGGCAT
GCTGGGGATGCGGTGGGCTCTATGGCTTCTGAGGCGGAAAGAACCAGCTG
GGGCTCGACAGCTCGACTCTAGaATTGCTTCCTCGCTCACTGACTCGCTG
CGCTCGGTCGTTCGGCTGCGGCGAGCGGTATCAGCTCACTCAAAGGCGGT
AATACGGTTATCCACAGAATCAGGGGATAACGCAGGAAAGAACATGTGAG
CAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTC
AAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGT
AACTATCGTCTTGAGTCCAACCCGGTAAGACACGACTTATCGCCACTGGC
AGCAGCCACTGGTAACAGGATTAGCAGAGCGAGGTATGTAGGCGGTGCTA
CAGAGTTCTTGAAGTGGTGGCCTAACTACGGCTACACTAGAAGAACAGTA
TTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCT
TTGATCTTTTCTACGGGGTCTGACGCTCAGTGGAACGAAAACTCACGTTA
AGGGATTTTGGTCATGAGATTATCAAAAAGGATCTTCACCTAGATCCTTT
TAAATTAAAAATGAAGTTTTAAATCAATCTAAAGTATATATGAGTAAACT
GGTCTGACAGTTACCAATGCTTAATCAGTGAGGCACCTATCTCAGCGAT
CTGTCTATTTCGTTCATCCATAGTTGCCTGACTC

HTN-M-CO
Optimized DNA of M segment
SEQ ID NO. 2
ATGGGCATCTGGAAGTGGCTGGTCATGGCTAGCCTCGTGTGGCCCGTGCT

GACCCTGCGGAACGTGTACGACATGAAGATCGAGTGCCCCCACACCGTGT

-continued

CCTTCGGCGAGAACAGCGTGATCGGCTACGTGGAACTGCCCCCCGTGCCC

CTGGCCGATACAGCTCAGATGGTGCCCGAGAGCAGCTGCAGCATGGACAA

CCACCAGAGCCTGAACACCATCACCAAGTACACCCAGGTGTCCTGGCGGG

GCAAGGCCGATCAGAGCCAGAGCAGCCAGAACAGCTTCGAGACAGTGTCT

ACCGAGGTGGACCTGAAGGGCACCTGTGCCCTGAAGCACAAGATGGTGGA

AGAGAGCTACCGGTCCAGAAAGAGCGTGACCTGCTACGACCTGAGCTGCA

ACAGCACCTACTGCAAGCCCACCCTGTACATGATCGTGCCCATCCACGCC

TGCAACATGATGAAGTCCTGCCTGATCGCCCTGGGCCCCTACAGAGTGCA

GGTCGTGTACGAGCGGAGCTACTGCATGACCGGCGTGCTGATCGAGGGCA

AGTGCTTCGTGCCCGACCAGAGCGTGGTGTCCATCATCAAGCACGGCATC

TTCGATATCGCCAGCGTGCACATCGTGTGCTTTTTCGTGGCCGTCAAGGG

CAACACCTACAAGATTTTCGAGCAGGTCAAAAAGAGCTTCGAGAGCACCT

GTAACGACACCGAGAACAAGGTGCAGGGCTACTACATCTGCATCGTGGGC

GGCAACAGCGCCCCCATCTACGTGCCCACCCTGGACGACTTCCGGTCCAT

GGAAGCCTTCACCGGCATCTTCAGAAGCCCCCACGGCGAGGACCACGACC

TGGCCGGCGAGGAAATCGCCAGCTACTCCATCGTGGGCCCTGCCAACGCC

AAGGTGCCACACAGCGCCAGCAGCGACACCCTGTCCCTGATCGCCTACAG

CGGCATCCCCAGCTACAGCAGCCTGAGCATCCTGACCAGCAGCACCGAGG

CCAAGCACGTGTTCAGCCCTGGCCTGTTCCCCAAGCTGAACCACACCAAC

TGCGACAAGAGCGCCATCCCCCTGATCTGGACCGGCATGATCGACCTGCC

CGGCTACTACGAGGCCGTGCACCCCTGCACCGTGTTCTGCGTGCTGTCTG

GCCCTGGAGCCAGCTGCGAGGCCTTTTCTGAGGGCGGCATCTTTAACATC

ACCAGCCCCATGTGCCTGGTGTCCAAGCAGAACCGGTTCCGGCTGACCGA

GCAGCAGGTCAACTTCGTGTGCCAGCGGGTGGACATGGACATCGTGGTGT

ACTGCAACGGCCAGCGGAAAGTGATCCTGACCAAGACCCTCGTGATCGGC

CAGTGCATCTACACCATCACAAGCCTGTTCAGCCTGCTGCCCGGCGTGGC

CCACTCTATCGCCGTGGAACTGTGCGTGCCCGGCTTTCACGGCTGGGCCA

CAGCTGCCCTGCTGGTCACCTTCTGCTTCGGCTGGGTGCTGATCCCCGCC

ATCACCTTCATCATCCTGACCGTGCTGAAGTTTATCGCCAACATCTTCCA

CACCAGCAACCAGGAAAACCGGCTCAAGTCCGTGCTGCGGAAGATCAAAG

AGGAATTCGAAAAGACCAAGGGCAGCATGGTCTGCGACGTGTGCAAATAC

GAGTGCGAGACATACAAAGAGCTGAAGGCCCACGGCGTGTCCTGCCCTCA

GAGCCAGTGCCCCTACTGCTTCACCCACTGCGAGCCTACCGAGGCCGCCT

TCCAGGCCCACTACAAAGTGTGCCAGGTCACACACCGGTTCAGGGACGAC

CTGAAGAAAACCGTGACCCCCCAGAACTTCACCCCCGGCTGCTACCGGAC

CCTGAACCTGTTCCGGTACAAGAGCCGGTGCTACATCTTTACCATGTGGA

TCTTTCTGCTGGTGCTCGAGTCCATCCTGTGGGCCGCCAGCGCCAGCGAA

ACCCCTCTGACCCCCGTGTGGAACGACAACGCCCATGGCGTGGGCTCTGT

GCCCATGCACACCGACCTGGAACTGGACTTCAGCCTGACCAGCTCCAGCA

AGTACACCTACCGGCGGAAGCTGACCAACCCCCTGGAAGAGGCCCAGAGC

ATCGACCTGCACATCGAGATCGAGGAACAGACCATCGGAGTCGATGTCCA

-continued

```
CGCCCTGGGACATTGGTTCGACGGACGGCTGAACCTGAAAACCAGCTTCC
ACTGCTACGGCGCCTGCACTAAGTACGAGTACCCCTGGCACACCGCCAAG
TGCCACTACGAGCGGGACTACCAGTACGAGACAAGCTGGGGCTGTAACCC
CAGCGACTGTCCAGGCGTGGGCACCGGCTGTACAGCTTGTGGCCTGTACC
TGGACCAGCTGAAGCCCGTGGGCTCCGCCTACAAGATCATCACCATCCGG
TACAGCAGACGCGTGTGCGTGCAGTTCGGCGAAGAGAACCTGTGCAAGAT
CATCGACATGAACGACTGCTTCGTGTCCCGGCACGTGAAAGTGTGCATCA
TCGGCACCGTGTCCAAGTTCAGCCAGGGCGATACCCTGCTGTTCTTCGGC
CCTCTGGAAGGCGGCGGACTGATCTTCAAGCACTGGTGCACAAGCACCTG
TCAGTTTGGCGACCCCGGCGACATCATGAGCCCCAGAGACAAGGGCTTCC
TGTGCCCCGAGTTCCCCGGCAGCTTCCGGAAGAAGTGCAACTTCGCCACC
ACCCCCATCTGCGAGTACGACGGCAACATGGTGTCCGGCTACAAGAAAGT
GATGGCCACCATCGACAGCTTCCAGAGCTTCAACACCTCCACCATGCACT
TCACCGACGAGCGGATCGAGTGGAAGGACCCCGACGGCATGCTGCGGGAC
CACATCAACATCCTGGTCACCAAGGACATCGACTTCGACAACCTGGGCGA
GAACCCCTGCAAGATCGGCCTGCAGACCTCCAGCATCGAGGGCGCTTGGG
GCAGCGGCGTGGGCTTTACCCTGACCTGTCTGGTGTCCCTGACCGAGTGC
CCCACCTTCCTGACCTCCATCAAGGCCTGCGACAAGGCCATCTGTTACGG
CGCCGAGTCCGTGACCCTGACAAGAGGCCAGAACACCGTGAAGGTGTCCG
GCAAAGGCGGCCACAGCGGCAGCACCTTCAGATGCTGCCACGGGGAGGAC
TGCAGCCAGATCGGACTGCATGCCGCAGCACCCCACCTGGACAAAGTGAA
CGGCATCAGCGAGATCGAGAACTCCAAGGTGTACGACGATGGCGCCCCTC
AGTGCGGCATCAAGTGTTGGTTCGTGAAGTCCGGCGAGTGGATCAGCGGC
ATCTTCTCCGGCAACTGGATCGTGCTGATTGTGCTGTGCGTGTTCCTGCT
GTTTAGCCTGGTGCTGCTGAGCATTCTGTGTCCCGTGCGCAAGCACAAGA
AAAGCTGATGA
``` pWRG7077
plasmid

SEQ ID NO. 3

```
GGGGGGGGGGGGCGCTGAGGTCTGCCTCGTGAAGAAGGTGTTGCTGACTC
ATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTT
TGCTTTGCCACGGAACGGTCTGCGTTGTCGGGAAGATGCGTGATCTGATC
CTTCAACTCAGCAAAAGTTCGATTTATTCAACAAAGCCGCCGTCCCGTCA
AGTCAGCGTAATGCTCTGCCAGTGTTACAACCAATTAACCAATTCTGATT
AGAAAAACTCATCGAGCATCAAATGAAACTGCAATTTATTCATATCAGGA
TTATCAATACCATATTTTTGAAAAAGCCGTTTCTGTAATGAAGGAGAAAA
CTCACCGAGGCAGTTCCATAGGATGGCAAGATCCTGGTATCGGTCTGCGA
TTCCGACTCGTCCAACATCAATACAACCTATTAATTTCCCCTCGTCAAAA
ATAAGGTTATCAAGTGAGAAATCACCATGAGTGACGACTGAATCCGGTGA
GAATGGCAAAAGCTTATGCATTTCTTTCCAGACTTGTTCAACAGGCCAGC
CATTACGCTCGTCATCAAAATCACTCGCATCAACCAAACCGTTATTCATT
```

-continued

```
CGTGATTGCGCCTGAGCGAGACGAAATACGCGATCGCTGTTAAAAGGACA
ATTACAAACAGGAATCGAATGCAACCGGCGCAGGAACACTGCCAGCGCAT
CAACAATATTTTCACCTGAATCAGGATATTCTTCTAATACCTGGAATGCT
GTTTTCCCGGGGATCGCAGTGGTGAGTAACCATGCATCATCAGGAGTACG
GATAAAATGCTTGATGGTCGGAAGAGGCATAAATTCCGTCAGCCAGTTTA
GTCTGACCATCTCATCTGTAACATCATTGGCAACGCTACCTTTGCCATGT
TTCAGAAACAACTCTGGCGCATCGGGCTTCCCATACAATCGATAGATTGT
CGCACCTGATTGCCCGACATTATCGCGAGCCCATTTATACCCATATAAAT
CAGCATCCATGTTGGAATTTAATCGCGGCCTCGAGCAAGACGTTTCCCGT
TGAATATGGCTCATAACACCCCTTGTATTACTGTTTATGTAAGCAGACAG
TTTTATTGTTCATGATGATATATTTTTATCTTGTGCAATGTAACATCAGA
GATTTTGAGACACAACGTGGCTTTCCCCCCCCCCCGGCATGCCTGCAGG
TCGACAATATTGGCTATTGGCCATTGCATACGTTGTATCTATATCATAAT
ATGTACATTTATATTGGCTCATGTCCAATATGACCGCCATGTTGACATTG
ATTATTGACTAGTTATTAATAGTAATCAATTACGGGGTCATTAGTTCATA
GCCCATATATGGAGTTCCGCGTTACATAACTTACGGTAAATGGCCCGCCT
GGCTGACCGCCCAACGACCCCCGCCCATTGACGTCAATAATGACGTATGT
TCCCATAGTAACGCCAATAGGGACTTTCCATTGACGTCAATGGGTGGAGT
ATTTACGGTAAACTGCCCACTTGGCAGTACATCAAGTGTATCATATGCCA
AGTCCGCCCCCTATTGACGTCaATGACGGTAAATGGCCCGCCTGGCATTA
TGCCCAGTACATGACCTTACGGGACTTTCCTACTTGGCAGTACATCTACG
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTACAGGATGGG
GTCCCATTTATTATTTACAAATTCACATATACAACAACGCCGTCCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
CCGAGCCCTGGTCCCATGCCTCCAGCGGCTCATGGTCGCTCGGCAGCTCC
TTGCTCCTAACAGTGGAGGCCAGACTTAGGCACAGCACAATGCCCACCAC
CACCAGTGTGCCGCACAAGGCCGTGGCGGTAGGGTATGTGTCTGAAAATG
AGCTCGGAGATTGGGCTCGCACCGCTGACGCAGATGGAAGACTTAAGGCA
```

-continued
GCGGCAGAAGAAGATGCAGGCAGCTGAGTTGTTGTATTCTGATAAGAGTC

AGAGGTAACTCCCGTTGCGGTGCTGTTAACGGTGGAGGGCAGTGTAGTCT

GAGCAGTACTCGTTGCTGCCGCGCGCGCCACCAGACATAATAGCTGACAG

ACTAACAGACTGTTCCTTTCCATGGGTCTTTTCTGCAGTCACCGTCCAAG

CTTGCGGCCGCCACCAGATCTACGTATGATCAGCCTCGACTGTGCCTTCT

AGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCAT

CGCATTGTCTGAGTAGGTGTCATTCTATTCTGGGGGGTGGGGTGGGGCAG

GACAGCAAGGGGAGGATTGGGAAGACAATAGCAGGCATGCTGGGGATGC

GGTGGGCTCTATGGCTTCTGAGGCGGAAAGAACCAGCTGGGGCTCGACAG

CTCGACTCTAGaATTGCTTCCTCGCTCACTGACTCGCTGCGCTCGGTCGT

TCGGCTGCGGCGAGCGGTATCAGCTCACTCAAAGGCGGTAATACGGTTAT

CCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGT

GGCGAAACCCGACAGGACTATAAAGATACCAGGCGTTTCCCCCTGGAAGC

TCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCT

TGAGTCCAACCCGGTAAGACACGACTTATCGCCACTGGCAGCAGCCACTG

GTAACAGGATTAGCAGAGCGAGGTATGTAGGCGGTGCTACAGAGTTCTTG

AAGTGGTGGCCTAACTACGGCTACACTAGAAGAACAGTATTTGGTATCTG

CGCTCTGCTGAAGCCAGTTACCTTCGGAAAAAGAGTTGGTAGCTCTTGAT

CCGGCAAACAAACCACCGCTGGTAGCGGTGGTTTTTTTGTTTGCAAGCAG

CAGATTACGCGCAGAAAAAAAGGATCTCAAGAAGATCCTTTGATCTTTTC

TACGGGGTCTGACGCTCAGTGGAACGAAAACTCACGTTAAGGGATTTTGG

TCATGAGATTATCAAAAGGATCTTCACCTAGATCCTTTTAAATTAAAAA

TGAAGTTTTAAATCAATCTAAAGTATATATGAGTAAACTTGGTCTGACAG

TTACCAATGCTTAATCAGTGAGGCACCTATCTCAGCGATCTGTCTATTTC

GTTCATCCATAGTTGCCTGACTC

SEQ ID NO. 4
Bgl II cloning site
AGATCT

SEQ ID NO. 5
Not I cloning site
GCGGCCGC

REFERENCES

1. Hooper J W, Li D. Vaccines against hantaviruses. Curr Top Microbiol Immunol 2001; 256: 171-91.
2. Maes P, Clement J, Van Ranst M. Recent approaches in hantavirus vaccine development. Expert Rev Vaccines 2009; 8 (January (1)):67-76.
3. Wang Q, Zhou H, Han Y H, Wang X F, Wang S W, Yin W W, et al. Epidemiology and surveillance programs on hemorrhagic fever with renal syndrome in Mainland China, 2005-2008. Zhonghua Liu Xing Bing Xue Za Zhi 2010; 31 (June(6)):675-80.
4. Fang L Q, Wang X J, Liang S, Li Y L, Song S X, Zhang W Y, et al. Spatiotemporal trends and climatic factors of hemorrhagic fever with renal syndrome epidemicin Shandong Province, China. PLoS Negl Trop Dis 2010; 4 (8):e789.
5. Zhang Y Z, Zou Y, Fu Z F, Plyusnin A. *Hantavirus* infections in humans and animals, China. Emerg Infect Dis August 2010; 16 (August (8)):1195-203.
6. Heyman P, Vaheri A. Situation of hantavirus infections and haemorrhagic fever with renal syndrome in European countries as of December 2006. Euro Survel 12008; 13 (July (28)).
7. Chu Y K, Jennings G B, Schmaljohn C S. A vaccinia virus-vectored Hantaan virus vaccine protects hamsters from challenge with Hantaan and Seoul viruses but not Puumala virus. J Virol 1995; 69 (October (10)):6417-23.
8. Hooper J W, Custer D M, Thompson E, Schmaljohn C S. DNA vaccination with the Hantaan virus M gene protects hamsters against three of four HFRS Nanta viruses and elicits a high-titer neutralizing antibody response in Rhesus monkeys. J Virol 2001; 75 (September (18)):8469-77.
9. McClain D J, Summers P L, Harrison S A, Schmaljohn A L, Schmaljohn C S. Clinical evaluation of a vaccinia-vectored Hantaan virus vaccine. J Med Virol 2000; 60 (January (1)):77-85.
10. Schmaljohn C S, Hasty S E, Dalrymple J M. Preparation of candidate vaccinia-vectored vaccines for haemorrhagic fever with renal syndrome. Vaccine 1992; 10 (1): 10-3.
11. Schmaljohn C S, Chu Y K, Schmaljohn A L, Dalrymple J M. Antigenic subunits of Hantaan virus expressed by baculovirus and vaccinia virus recombinants. J Virol 1990; 64 (July (7)):3162-70.
12. Custer D M, Thompson E, Schmaljohn C S, Ksiazek T G, Hooper J W. Active and passive vaccination against hantavirus pulmonary syndrome with Andesvirus M genome segment-based DNA vaccine. J Virol 2003; 77 (September(18)):9894-905.
13. Hooper J W, Kamrud K I, Elgh F, Custer D, Schmaljohn C S. DNA vaccination with hantavirus M segment elicits neutralizing antibodies and protects against Seoul virus infection. Virology 1999; 255 (March (2)):269-78.
14. Schmaljohn C, Vanderzanden L, Bray M, Custer D, Meyer B, Li D, et al. Naked DNAvaccines expressing the prM and E genes of Russian spring summer encephalitis virus and Central European encephalitis virus protect mice from homologous and heterologous challenge. J Virol 1997; 71 (December (12)):9563-9.
15. Hooper J W, inventor; United States of America, assignee. Puumala Virus Full-Length M Segment-Based DNA Vaccine. United States Patent ApplicationUS20100323024,2010 December 23.
16. Roy M J, Wu M S, Barr L J, Fuller J T, Tussey L G, Speller S, et al. Induction of antigen-specific CD8+ T cells, T helper cells, and protective levels of antibody in humans by particle-mediated administration of a hepatitis B virus DNA vaccine. Vaccine 2000; 19 (November (7-8)):764-78.
17. Roberts L K, Barr L J, Fuller D H, McMahon C W, Leese P T, Jones S. Clinical safety and efficacy of a powdered hepatitis B nucleic acid vaccine delivered to the epidermis by a commercial prototype device. Vaccine 2005; 23 (September(40)):4867-78.
18. Badger C V, Richardson J D, Dasilva R L, Richards M J, Josleyn M D, Dupuy L C, et al. Development and application of a flow cytometric potency assay for DNA vaccines. Vaccine 2011; (January):6728-35.
19. Rossi C A, Ksiazek T G. Enzyme-linked immunoborbent assay (ELISA). In: Lee H W, Calisher C, Schmaljohn C, editors. Manual of hemorrhagic fever with renal k syndrome and hantavirus pulmonary syndrome. Seoul, Korea: WHO Collaborating Center for Virus Reference and Research (Hantaviruses), Asan Institute for Life Sciences; 1999. p. 87-98.
20. Schmaljohn C S, Hasty S E, Dalrymple J M, LeDuc J W, Lee H W, von Bonsdorff C H, et al. Antigenic and genetic properties of viruses linked to hemorrhagic fever with renal syndrome. Science 1985; 227 (March (4690)):1041-4.
21. Chu Y K, Jennings G, Schmaljohn A, Elgh F, Hjelle B, Lee H W, et al. Cross-neutralization of hantaviruses with immune sera from experimentally infected animals and from hemorrhagic fever with renal syndrome and hantavirus pulmonary syndrome patients. J Infect Dis 1995; 172 (December (6)):1581-4.
22. Chu Y K, Rossi C, Leduc J W, Lee H W, Schmaljohn C S, Dalrymple J M. Serological relationships among viruses in the *Hantavirus* genus, family Bunyaviridae. Virology 1994; 198 (January (1)):196-204.
23. Fuller D H, Loudon P, Schmaljohn C. Preclinical and clinical progress of particle-mediated DNA vaccines for infectious diseases. Methods 2006; 40 (September(1)):86-97.
24. Hooper J W, Custer D M, Smith J, Wahl-Jensen V. Hantaan/Andes virus DNA vaccine elicits a broadly cross-reactive neutralizing antibody response in non-human primates. Virology 2006; 347 (March (1)):208-16.
25. Spik K W, Badger C, Mathiessen I, Tjelle T, Hooper J W, Schmaljohn C. Mixing of M segment DNA vaccines to Hantaan virus and Puumala virus reduces their immunogenicity in hamsters. Vaccine 2008; 26 (September (40)): 5177-81.
26. Sheshberadaran H, Niklasson B, Tkachenko E A. Antigenic relationship between hantaviruses analysed by immunoprecipitation. J Gen Virol 1988; 69 (March (Pt10)):2645-51.
27. Arikawa J, Schmaljohn A L, Dalrymple J M, Schmaljohn C S. Characterization of Hantaan virus envelope glycoprotein antigenic determinants defined by monoclonal antibodies. J Gen Virol 1989; 70 (March (Pt 3)):615-24.
28. Che Yk, et al., A vaccine virus-vectored Hantaan virus vaccine protects hamsters from challenge with Hantaan and Seoul viruses but not Puumala virus. J. Virol 1995 October; 69 (10):6417-23.
29. Hooper et al, DNA vaccination with the Hantaan virus M gene protects Hamsters against three of four HFRS hantaviruses and elicits a high-titer neutralizing antibody response in Rhesus monkeys. J Virol 2001, September; 75 (18):8469-77.
30. Schmaljohn, et al., Naked DNA vaccines expressing the preM and E genes of Russian spring summer encephalitis virus and Central European encephalitis virus protect mice from homologous and heterologous challenge. J Virol 1997 December; 71 (12):9563-9.
31. Spik, et al., Mixing of immunogenicity in hamsters. Vaccine 2008 September 19; 26 (40):5177-81.
32. Brocato, R. L., M. J. Josleyn, et al. (2013). "Construction and nonclinical testing of a puumala virus synthetic m gene-based DNA vaccine." Clin Vaccine Immunol 20 (2): 218-226

What is claimed is:

1. A bivalent vaccine for HTNV and PUUV that protects against HFRS caused by HTNV infection comprising a synthetic codon-optimized HTNV full-length M gene open reading frame segment of SEQ ID NO. 1 and PUUV DNA vaccine.

2. The bivalent vaccine of claim 1, wherein immunogenic amounts of said open reading frame of SEQ ID No. 1 and said PUUV DNA are administered using intramuscular or intradermal delivery devices.

3. The bivalent vaccine for HTNV and PUUV of claim 1, wherein said PUUV DNA is optimized in dose and delivery schedule.

* * * * *

SEQUENCE LISTING

```
<160> NUMBER OF SEQ ID NOS: 5

<210> SEQ ID NO 1
<211> LENGTH: 7634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360 catattttg aaaaagccgt ttctgtaatg aaggagaaaa ctcaccgagg cagttccata     420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
aatccggtga gaatggcaaa agcttatgca tttctttcca gacttgttca acaggccagc     600
cattacgctc gtcatcaaaa tcactcgcat caaccaaacc gttattcatt cgtgattgcg     660
cctgagcgag acgaaatacg cgatcgctgt taaaaggaca attacaaaca ggaatcgaat     720
```

```
gcaaccggcg caggaacact gccagcgcat caacaatatt ttcacctgaa tcaggatatt    780
cttctaatac ctggaatgct gttttcccgg ggatcgcagt ggtgagtaac catgcatcat    840
caggagtacg ataaaatgc ttgatggtcg gaagaggcat aaattccgtc agccagttta     900
gtctgaccat ctcatctgta acatcattgg caacgctacc tttgccatgt ttcagaaaca    960
actctggcgc atcgggcttc ccatacaatc gatagattgt cgcacctgat tgcccgacat   1020
tatcgcgagc ccatttatac ccatataaat cagcatccat gttggaattt aatcgcggcc   1080
tcgagcaaga cgtttcccgt tgaatatggc tcataacacc ccttgtatta ctgtttatgt   1140
aagcagacag ttttattgtt catgatgata tattttatc ttgtgcaatg taacatcaga    1200
gattttgaga cacaacgtgg ctttccccc ccccccggca tgcctgcagg tcgacaatat    1260
tggctattgg ccattgcata cgttgtatct atatcataat atgtacattt atattggctc   1320
atgtccaata tgaccgccat gttgacattg attattgact agttattaat agtaatcaat   1380
tacgggtca ttagttcata gcccatatat ggagttccgc gttacataac ttacggtaaa    1440
tggcccgcct ggctgaccgc ccaacgaccc ccgcccattg acgtcaataa tgacgtatgt   1500
tcccatagta acgccaatag ggactttcca ttgacgtcaa tgggtggagt atttacggta   1560
aactgcccac ttggcagtac atcaagtgta tcatatgcca gtccgcccc ctattgacgt    1620
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acccccttt    2100
ggctcttatg catgctatac tgttttggc ttggggccta tacaccccg cttccttatg     2160
ctataggtga tggtatagct tagcctatag gtgtgggtta ttgaccatta ttgaccactc   2220
ccctattggt gacgatactt tccattacta atccataaca tggctctttg ccacaactat   2280
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg ccaccatggg catctggaag tggctggtca   2940
tggctagcct cgtgtgggcc gtgctgaccc tgcggaacgt gtacgacatg aagatcgagt   3000
gcccccacac cgtgtccttc ggcgagaaca gcgtgatcgg ctacgtggaa ctgccccccg   3060
tgccctggc cgatacagct cagatggtgc ccgagagcag ctgcagcatg gacaaccacc    3120
```

```
agagcctgaa caccatcacc aagtacaccc aggtgtcctg gcggggcaag gccgatcaga    3180
gccagagcag ccagaacagc ttcgagacag tgtctaccga ggtggacctg aagggcacct    3240
gtgccctgaa gcacaagatg gtggaagaga gctaccggtc cagaaagagc gtgacctgct    3300
acgacctgag ctgcaacagc acctactgca agcccaccct gtacatgatc gtgcccatcc    3360
acgcctgcaa catgatgaag tcctgcctga tcgccctggg ccccctacaga gtgcaggtcg    3420 tgtacgagcg gagctactgc atgaccggcg tgctgatcga gggcaagtgc ttcgtgcccg    3480
accagagcgt ggtgtccatc atcaagcacg gcatcttcga tatcgccagc gtgcacatcg    3540
tgtgcttttt cgtggccgtc aagggcaaca cctacaagat tttcgagcag gtcaaaaaga    3600
gcttcgagag cacctgtaac gacaccgaga acaaggtgca gggctactac atctgcatcg    3660
tgggcggcaa cagcgccccc atctacgtgc ccaccctgga cgacttccgg tccatggaag    3720
ccttcaccgg catcttcaga agcccccacg gcgaggacca cgacctggcc ggcgaggaaa    3780
tcgccagcta ctccatcgtg ggccctgcca acgccaaggt gccacacagc gccagcagcg    3840
acaccctgtc cctgatcgcc tacagcggca tccccagcta cagcagcctg agcatcctga    3900
ccagcagcac cgaggccaag cacgtgttca gccctggcct gttccccaag ctgaaccaca    3960
ccaactgcga caagagcgcc atccccctga tctggaccgg catgatcgac ctgcccggct    4020
actacgaggc cgtgcacccc tgcaccgtgt tctgcgtgct gtctggccct ggagccagct    4080
gcgaggcctt ttctgagggc ggcatcttta acatcaccag ccccatgtgc ctggtgtcca    4140
agcagaaccg gttccggctg accgagcagc aggtcaactt cgtgtgccag cgggtggaca    4200
tggacatcgt ggtgtactgc aacggccagc ggaaagtgat cctgaccaag accctcgtga    4260
tcggccagtg catctacacc atcacaagcc tgttcagcct gctgcccggc gtggcccact    4320
ctatcgccgt ggaactgtgc gtgcccggct tcacggctg gccacagct gccctgctgg    4380 tcaccttctg cttcggctgg gtgctgatcc ccgccatcac cttcatcatc ctgaccgtgc    4440 tgaagttat cgccaacatc ttccacacca gcaaccagga aaaccggctc aagtccgtgc    4500
tgcggaagat caaagaggaa ttcgaaaaga ccaagggcag catggtctgc gacgtgtgca    4560
aatacgagtg cgagacatac aaaagagctga aggcccacgg cgtgtcctgc cctcagagcc    4620
agtgccccta ctgcttcacc cactgcgagc ctaccgaggc cgccttccag gcccactaca    4680
aagtgtgcca ggtcacacac cggttcaggg acgacctgaa gaaaccgtg accccccaga    4740 acttcacccc cggctgctac cggaccctga acctgttccg gtacaagagc cggtgctaca    4800 tcttaccat gtggatcttt ctgctggtgc tcgagtccat cctgtgggcc gccagcgcca    4860
gcgaaacccc tctgaccccc gtgtggaacg acaacgccca tggcgtgggc tctgtgccca    4920
tgcacaccga cctggaactg gacttcagcc tgaccagctc cagcaagtac acctaccggc    4980
ggaagctgac caacccctg aagagagccc agagcatcga cctgcacatc gagatcgagg    5040
aacagaccat cggagtcgat gtccacgccc tgggacattg gttcgacgga cggctgaacc    5100
tgaaaaccag cttccactgc tacggcgcct gcactaagta cgagtacccc tggcacaccg    5160
ccaagtgcca ctacgagcgg gactaccagt acgagacaag ctgggctgt aaccccagcg    5220 actgtccagg cgtgggcacc ggctgtacag cttgtggcct gtacctggac cagctgaagc    5280
ccgtgggctc cgcctacaag atcatcacca tccggtacag cagacgcgtg tgcgtgcagt    5340
tcggcgaaga gaacctgtgc aagatcatcg acatgaacga ctgcttcgtg tcccggcacg    5400
tgaaagtgtg catcatcggc accgtgtcca agttcagcca gggcgatacc ctgctgttct    5460
tcggccctct ggaaggcggc ggactgatct tcaagcactg gtgcacaagc acctgtcagt    5520
```

| | |
|---|---|
| ttggcgaccc cggcgacatc atgagcccca gagacaaggg cttcctgtgc cccgagttcc | 5580 |
| ccggcagctt ccggaagaag tgcaacttcg ccaccacccc catctgcgag tacgacggca | 5640 |
| acatggtgtc cggctacaag aaagtgatgg ccaccatcga cagcttccag agcttcaaca | 5700 |
| cctccaccat gcacttcacc gacgagcgga tcgagtggaa ggaccccgac ggcatgctgc | 5760 |
| gggaccacat caacatcctg gtcaccaagg acatcgactt cgacaacctg ggcgagaacc | 5820 |
| cctgcaagat cggcctgcag acctccagca tcgagggcgc ttggggcagc ggcgtgggct | 5880 |
| ttaccctgac ctgtctggtg tccctgaccg agtgccccac cttcctgacc tccatcaagg | 5940 |
| cctgcgacaa ggccatctgt tacgcgccg agtccgtgac cctgacaaga ggccagaaca | 6000 |
| ccgtgaaggt gtccggcaaa gcggccaca gcggcagcac cttcagatgc tgccacgggg | 6060 |
| aggactgcag ccagatcgga ctgcatgccg cagcacccca cctggacaaa gtgaacggca | 6120 |
| tcagcgagat cgagaactcc aaggtgtacg acgatggcgc ccctcagtgc ggcatcaagt | 6180 |
| gttggttcgt gaagtccggc gagtggatca gcggcatctt ctccggcaac tggatcgtgc | 6240 |
| tgattgtgct gtgcgtgttc ctgctgttta gcctggtgct gctgagcatt ctgtgtcccg | 6300 |
| tgcgcaagca caagaaaagc tgatgaagat ctacgtatga tcagcctcga ctgtgccttc | 6360 |
| tagttgccag ccatctgttg tttgcccctc cccgtgcct tccttgaccc tggaaggtgc | 6420 |
| cactcccact gtccttcct aataaaatga ggaaattgca tcgcattgtc tgagtaggtg | 6480 |
| tcattctatt ctggggggtg gggtggggca ggacagcaag ggggaggatt gggaagacaa | 6540 |
| tagcaggcat gctggggatg cggtgggctc tatggcttct gaggcggaaa gaaccagctg | 6600 |
| gggctcgaca gctcgactct agaattgctt cctcgctcac tgactcgctg cgctcggtcg | 6660 |
| ttcggctgcg gcgagcggta tcagctcact caaaggcggt aatacggtta tccacagaat | 6720 |
| caggggataa cgcaggaaag aacatgtgag caaaaggcca gcaaaaggcc aggaaccgta | 6780 |
| aaaaggccgc gttgctggcg ttttccata ggctccgccc ccctgacgag catcacaaaa | 6840 |
| atcgacgctc aagtcagagg tggcgaaacc cgacaggact ataaagatac caggcgtttc | 6900 |
| cccctggaag ctccctcgtg cgctctcctg ttccgaccct gccgcttacc ggatacctgt | 6960 |
| ccgcctttct cccttcggga agcgtggcgc tttctcatag ctcacgctgt aggtatctca | 7020 |
| gttcggtgta ggtcgttcgc tccaagctgg gctgtgtgca cgaaccccc gttcagcccg | 7080 |
| accgctgcgc cttatccggt aactatcgtc ttgagtccaa cccggtaaga cacgacttat | 7140 |
| cgccactggc agcagccact ggtaacagga ttagcagagc gaggtatgta ggcggtgcta | 7200 |
| cagagttctt gaagtggtgg cctaactacg gctacactag aagaacagta tttggtatct | 7260 |
| gcgctctgct gaagccagtt accttcggaa aaagagttgg tagctcttga tccgcaaac | 7320 |
| aaaccaccgc tggtagcggt ggtttttttg tttgcaagca gcagattacg cgcagaaaaa | 7380 |
| aaggatctca agaagatcct ttgatctttt ctacggggtc tgacgctcag tggaacgaaa | 7440 |
| actcacgtta agggatttg gtcatgagat tatcaaaaag gatcttcacc tagatccttt | 7500 |
| taaattaaaa atgaagtttt aaatcaatct aaagtatata tgagtaaact tggtctgaca | 7560 |
| gttaccaatg cttaatcagt gaggcaccta tctcagcgat ctgtctattt cgttcatcca | 7620 |
| tagttgcctg actc | 7634 |

<210> SEQ ID NO 2
<211> LENGTH: 3411
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | | | | | |
|---|---|---|---|---|---|
| atgggcatct | ggaagtggct | ggtcatggct | agcctcgtgt | ggcccgtgct | gaccctgcgg | 60 |
| aacgtgtacg | acatgaagat | cgagtgcccc | cacaccgtgt | ccttcggcga | aacagcgtg | 120 |
| atcggctacg | tggaactgcc | ccccgtgccc | ctggccgata | cagctcagat | ggtgcccgag | 180 |
| agcagctgca | gcatggacaa | ccaccagagc | ctgaacacca | tcaccaagta | cacccaggtg | 240 |
| tcctggcggg | gcaaggccga | tcagagccag | agcagccaga | acagcttcga | gacagtgtct | 300 |
| accgaggtgg | acctgaaggg | cacctgtgcc | ctgaagcaca | agatggtgga | agagagctac | 360 |
| cggtccagaa | agagcgtgac | ctgctacgac | ctgagctgca | acagcaccta | ctgcaagccc | 420 |
| accctgtaca | tgatcgtgcc | catccacgcc | tgcaacatga | tgaagtcctg | cctgatcgcc | 480 |
| ctgggcccct | acagagtgca | ggtcgtgtac | gagcggagct | actgcatgac | cggcgtgctg | 540 |
| atcgagggca | agtgcttcgt | gcccgaccag | agcgtggtgt | ccatcatcaa | gcacggcatc | 600 |
| ttcgatatcg | ccagcgtgca | catcgtgtgc | tttttcgtgg | ccgtcaaggg | caacacctac | 660 |
| aagatttccg | agcaggtcaa | aaagagcttc | gagagcacct | gtaacgacac | cgagaacaag | 720 |
| gtgcagggct | actacatctg | catcgtgggc | ggcaacagcg | cccccatcta | cgtgcccacc | 780 |
| ctggacgact | tccggtccat | ggaagccttc | accggcatct | tcagaagccc | cacggcgag | 840 |
| gaccacgacc | tggccggcga | ggaaatcgcc | agctactcca | tcgtgggccc | tgccaacgcc | 900 |
| aaggtgccac | acagcgccag | cagcgacacc | ctgtccctga | tcgcctacag | cggcatcccc | 960 |
| agctacagca | gcctgagcat | cctgaccagc | agcaccgagg | ccaagcacgt | gttcagccct | 1020 |
| ggcctgttcc | ccaagctgaa | ccacaccaac | tgcgacaaga | cgccatccc | cctgatctgg | 1080 |
| accggcatga | tcgacctgcc | cggctactac | gaggccgtgc | accctgcac | cgtgttctgc | 1140 |
| gtgctgtctg | gcctggagc | cagctgcgag | gccttttctg | agggcggcat | ctttaacatc | 1200 |
| accagcccca | tgtgcctggt | gtccaagcag | aaccggttcc | ggctgaccga | gcagcaggtc | 1260 |
| aacttcgtgt | gccagcgggt | ggacatggac | atcgtggtgt | actgcaacgg | ccagcggaaa | 1320 |
| gtgatcctga | ccaagaccct | cgtgatcggc | cagtgcatct | acaccatcac | aagcctgttc | 1380 |
| agcctgctgc | ccggcgtggc | ccactctatc | gccgtggaaa | ctgtgcgtgcc | cggctttcac | 1440 |
| ggctgggcca | cagctgccct | gctggtcacc | ttctgcttcg | gctgggtgct | gatccccgcc | 1500 |
| atcaccttca | tcatcctgac | cgtgctgaag | tttatcgcca | acatcttcca | caccagcaac | 1560 |
| caggaaaacc | ggctcaagtc | cgtgctgcgg | aagatcaaag | aggaattcga | aaagaccaag | 1620 |
| ggcagcatgg | tctgcgacgt | gtgcaaatac | gagtgcgaga | catacaaaga | gctgaaggcc | 1680 |
| cacggcgtgt | cctgccctca | gagccagtgc | ccctactgct | tcacccactg | cgagcctacc | 1740 |
| gaggccgcct | tccaggccca | ctacaaagtg | tgccaggtca | cacccggtt | cagggacgac | 1800 |
| ctgaagaaaa | ccgtgacccc | ccagaacttc | accccggct | gctaccggac | cctgaacctg | 1860 |
| ttccggtaca | agagccggtg | ctacatcttt | accatgtgga | tctttctgct | ggtgctcgag | 1920 |
| tccatcctgt | gggccgccag | cgccagcgaa | cccctctga | cccccgtgtg | gaacgacaac | 1980 |
| gcccatggcg | tgggctctgt | gcccatgcac | accgacctgg | aactggactt | cagcctgacc | 2040 |
| agctccagca | agtacaccta | ccggcggaag | ctgaccaacc | cctggaaga | ggcccagagc | 2100 |
| atcgacctgc | acatcgagat | cgaggaacag | accatcggag | tcgatgtcca | cgccctggga | 2160 |
| cattggttcg | acggacggct | gaacctgaaa | accagcttcc | actgctacgg | cgcctgcact | 2220 |

```
aagtacgagt acccctggca caccgccaag tgccactacg agcgggacta ccagtacgag    2280
acaagctggg gctgtaaccc cagcgactgt ccaggcgtgg gcaccggctg tacagcttgt    2340
ggcctgtacc tggaccagct gaagcccgtg gctccgcct acaagatcat caccatccgg     2400
tacagcagac gcgtgtgcgt gcagttcggc gaagagaacc tgtgcaagat catcgacatg    2460
aacgactgct tcgtgtcccg gcacgtgaaa gtgtgcatca tcggcaccgt gtccaagttc    2520
agccagggcg ataccctgct gttcttcggc cctctggaag gcggcggact gatcttcaag    2580
cactggtgca caagcacctg tcagtttggc gaccccggcg acatcatgag ccccagagac    2640
aagggcttcc tgtgccccga gttccccggc agcttccgga gaagtgcaa cttcgccacc     2700 acccccatct gcgagtacga cggcaacatg gtgtccggct acaagaaagt gatggccacc    2760
atcgacagct ccagagctt caacacctcc accatgcact tcaccgacga gcggatcgag     2820
tggaaggacc ccgacggcat gctgcgggac cacatcaaca tcctggtcac caaggacatc    2880
gacttcgaca acctgggcga gaaccccctgc aagatcggcc tgcagacctc cagcatcgag   2940
ggcgcttggg gcagcggcgt gggctttacc ctgacctgtc tggtgtccct gaccgagtgc    3000
cccaccttcc tgacctccat caaggcctgc gacaaggcca tctgttacgg cgccgagtcc    3060
gtgaccctga caagaggcca gaacaccgtg aaggtgtccg gcaaaggcgg ccacagcggc    3120
agcaccttca gatgctgcca cggggaggac tgcagccaga tcggactgca tgccgcagca    3180
ccccacctga caaagtgaa cggcatcagc gagatcgaga actccaaggt gtacgacgat     3240
ggcgcccctc agtgcggcat caagtgttgg ttcgtgaagt ccggcgagtg gatcagcggc    3300
atcttctccg gcaactggat cgtgctgatt gtgctgtgcg tgttcctgct gtttagcctg    3360
gtgctgctga gcattctgtg tcccgtgcgc aagcacaaga aaagctgatg a             3411
```

<210> SEQ ID NO 3
<211> LENGTH: 4223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggggggggggg ggcgctgagg tctgcctcgt gaagaaggtg ttgctgactc ataccaggcc    60
tgaatcgccc catcatccag ccagaaagtg agggagccac ggttgatgag agctttgttg    120
taggtggacc agttggtgat tttgaacttt tgctttgcca cggaacggtc tgcgttgtcg    180
ggaagatgcg tgatctgatc cttcaactca gcaaaagttc gatttattca acaaagccgc    240
cgtcccgtca gtcagcgta atgctctgcc agtgttacaa ccaattaacc aattctgatt     300
agaaaaactc atcgagcatc aaatgaaact gcaatttatt catatcagga ttatcaatac    360 catattttg aaaaagccgt ttctgtaatg aaggagaaaa ctcaccgagg cagttccata     420
ggatggcaag atcctggtat cggtctgcga ttccgactcg tccaacatca atacaaccta    480
ttaatttccc ctcgtcaaaa ataaggttat caagtgagaa atcaccatga gtgacgactg    540
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt taaaaggaca attacaaaca ggaatcgaat    720
gcaaccggcg caggaacact gccagcgcat caacaatatt ttcacctgaa tcaggatatt    780
cttctaatac ctggaatgct gttttcccgg ggatcgcagt ggtgagtaac catgcatcat    840
```

```
caggagtacg gataaaatgc ttgatggtcg gaagaggcat aaattccgtc agccagttta      900
gtctgaccat ctcatctgta acatcattgg caacgctacc tttgccatgt ttcagaaaca      960
actctggcgc atcgggcttc ccatacaatc gatagattgt cgcacctgat tgcccgacat     1020
tatcgcgagc ccatttatac ccatataaat cagcatccat gttggaattt aatcgcggcc     1080
tcgagcaaga cgtttcccgt tgaatatggc tcataacacc ccttgtatta ctgtttatgt     1140
aagcagacag ttttattgtt catgatgata tattttatc ttgtgcaatg taacatcaga      1200
gattttgaga cacaacgtgg cttccccccc cccccggca tgcctgcagg tcgacaatat      1260
tggctattgg ccattgcata cgttgtatct atatcataat atgtacattt atattggctc     1320
atgtccaata tgaccgccat gttgacattg attattgact agttattaat agtaatcaat     1380
tacgggtca ttagttcata gcccatatat ggagttccgc gttacataac ttacggtaaa      1440
tggcccgcct ggctgaccgc ccaacgaccc ccgcccattg acgtcaataa tgacgtatgt     1500
tcccatagta acgccaatag ggactttcca ttgacgtcaa tgggtggagt atttacggta     1560
aactgcccac ttggcagtac atcaagtgta tcatatgcca gtccgcccc ctattgacgt      1620
caatgacggt aaatggcccg cctggcatta tgcccagtac atgaccttac gggactttcc     1680
tacttggcag tacatctacg tattagtcat cgctattacc atggtgatgc ggttttggca     1740
gtacaccaat gggcgtggat agcggtttga ctcacgggga tttccaagtc tccaccccat     1800
tgacgtcaat gggagtttgt tttggcacca aaatcaacgg gactttccaa aatgtcgtaa     1860
taaccccgcc ccgttgacgc aaatgggcgg taggcgtgta cggtgggagg tctatataag     1920
cagagctcgt ttagtgaacc gtcagatcgc ctggagacgc catccacgct gttttgacct     1980
ccatagaaga caccgggacc gatccagcct ccgcggccgg gaacggtgca ttggaacgcg     2040
gattccccgt gccaagagtg acgtaagtac cgcctataga ctctataggc acacccctt     2100
ggctcttatg catgctatac tgttttggc ttggggccta tacacccccg cttccttatg      2160
ctataggtga tggtatagct tagcctatag gtgtgggtta ttgaccatta ttgaccactc     2220
ccctattggt gacgatactt tccattacta atccataaca tggctctttg ccacaactat     2280
ctctattggc tatatgccaa tactctgtcc ttcagagact gacacggact ctgtattttt     2340
acaggatggg gtcccatttta ttatttacaa attcacatat acaacaacgc cgtcccccgt    2400
gcccgcagtt tttattaaac atagcgtggg atctccacgc gaatctcggg tacgtgttcc     2460
ggacatgggc tcttctccgg tagcggcgga gcttccacat ccgagccctg gtcccatgcc     2520
tccagcggct catggtcgct cggcagctcc ttgctcctaa cagtggaggc cagacttagg     2580
cacagcacaa tgcccaccac caccagtgtg ccgcacaagg ccgtggcggt agggtatgtg     2640
tctgaaaatg agctcggaga ttgggctcgc accgctgacg cagatggaag acttaaggca     2700
gcggcagaag aagatgcagg cagctgagtt gttgtattct gataagagtc agaggtaact     2760
cccgttgcgg tgctgttaac ggtggagggc agtgtagtct gagcagtact cgttgctgcc     2820
gcgcgcgcca ccagacataa tagctgacag actaacagac tgttcctttc catgggtctt     2880
ttctgcagtc accgtccaag cttgcggccg ccaccagatc tacgtatgat cagcctcgac     2940
tgtgccttct agttgccagc catctgttgt ttgcccctcc ccgtgccttc cttgaccct      3000
ggaaggtgcc actcccactg tccttcccta ataaaatgag gaaattgcat cgcattgtct     3060
gagtaggtgt cattctattc tggggggtgg ggtggggcag gacagcaagg ggaggattg      3120
ggaagacaat agcaggcatg ctgggatgc ggtgggctct atggcttctg aggcggaaag      3180
aaccagctgg ggctcgacag ctcgactcta gaattgcttc ctcgctcact gactcgctgc     3240
```

```
gctcggtcgt tcggctgcgg cgagcggtat cagctcactc aaaggcggta atacggttat    3300
ccacagaatc aggggataac gcaggaaaga acatgtgagc aaaaggccag caaaaggcca    3360
ggaaccgtaa aaaggccgcg ttgctggcgt ttttccatag gctccgcccc cctgacgagc    3420
atcacaaaaa tcgacgctca agtcagaggt ggcgaaaccc gacaggacta taaagatacc    3480
aggcgtttcc ccctggaagc tccctcgtgc gctctcctgt tccgaccctg ccgcttaccg    3540
gatacctgtc cgcctttctc ccttcgggaa gcgtggcgct ttctcatagc tcacgctgta    3600
ggtatctcag ttcggtgtag gtcgttcgct ccaagctggg ctgtgtgcac gaaccccccg    3660
ttcagcccga ccgctgcgcc ttatccggta actatcgtct tgagtccaac ccggtaagac    3720
acgacttatc gccactggca gcagccactg gtaacaggat tagcagagcg aggtatgtag    3780
gcggtgctac agagttcttg aagtggtggc ctaactacgg ctacactaga agaacagtat    3840
ttggtatctg cgctctgctg aagccagtta ccttcggaaa aagagttggt agctcttgat    3900
ccggcaaaca accaccgct ggtagcggtg gttttttgt ttgcaagcag cagattacgc       3960
gcagaaaaaa aggatctcaa gaagatcctt tgatctttc tacggggtct gacgctcagt     4020
ggaacgaaaa ctcacgttaa gggattttgg tcatgagatt atcaaaaagg atcttcacct    4080
agatcctttt aaattaaaaa tgaagtttta aatcaatcta agtatatat gagtaaactt     4140 ggtctgacag ttaccaatgc ttaatcagtg aggcacctat ctcagcgatc tgtctatttc    4200
gttcatccat agttgcctga ctc                                             4223

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 agatct                                                                      6

<210> SEQ ID NO 5
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 gcggccgc                                                                    8
```